United States Patent [19]

Racaniello et al.

[11] Patent Number: 5,631,407

[45] Date of Patent: May 20, 1997

[54] TRANSGENIC MOUSE EXPRESSING DNA SEQUENCES ENCODING THE HUMAN POLIOVIRUS RECEPTOR

[75] Inventors: Vincent Racaniello, New York, N.Y.; Cathy Mendelsohn, Strasbourg, France; Frank Costantini, New York, N.Y.

[73] Assignee: The Trustees of Columbia University in the City of New York, New York, N.Y.

[21] Appl. No.: 182,371

[22] Filed: Jan. 14, 1994

Related U.S. Application Data

[63] Continuation of Ser. No. 495,744, Mar. 19, 1990, abandoned, which is a continuation-in-part of Ser. No. 321,957, Mar. 10, 1989, abandoned.

[51] Int. Cl.$^6$ .............................. C12N 5/00; C12N 15/00; C12P 15/00; A61K 49/00
[52] U.S. Cl. ............................ 800/2; 435/172.3; 424/9.1
[58] Field of Search ..................................... 800/2; 424/9

[56] References Cited

PUBLICATIONS

Scangos et al (1987) Advin Genetics 24, 285–322.
Mendelsoha et al (1986) Proced. Natl. Acad. Sci. 83, 7845–7849.
Seed et al (1987) Proced. Natl. Acad Sci. 84, 3365–3369.
Nobis et al (1985) J. Gen. Virol. 66, 2563–2569.
Subelt et al (1980) J. Neuropath. Expt. Neurol. 39, 138–148.
Seed et al (1987) Proc. Natl. Acad Sci 84, 3365–3369.
Hogan et al (1986) Manip. the Mouse Embryo, Cold Spring Harbor Lab, pp. 153–203.
Kohara et al (1988) J. Virol 62, 2828–2835.
Sublet (1980) J. Neruopath Expt. Neurol 39, 138–148.
Minor, P.D., Pipkin, P.A. Hockely, D., Schild, G.C. and Almond, J.W., Virus Research, 1, pp. 203–212 (1984).
Nobis, P., Zibirre, R., Meyer, G., Kuhe, J., Warneck, G., and Koch, G., J. Gen. Virol., 66, pp. 2563–2569 (1985).
Shepley, M.P., Sherry, B., and Weiner, H.L., P.N.A.S. USA, 85, pp. 7743–7747 (Oct. 1988).
Holland, J., Virology, 15, pp. 312–326 (1961).
Weis, W., Brown, J. H., Cusack, S., Paulson, J.C., Skehel, J. J. and Wiley, D.C., Nature, 333, pp. 426–431 (Jun. 1988).
Colonno, R.J., Condra, J.H., Mizutani, S., Callahan, P.L., Davies, M., and Murcko, M.A., P.N.A.S. USA, 85, pp. 5449–5453 (Aug. 1988).
Mendelsohn, C.L., Wimmer, E. and Rancaniello, V.R., Cell, 56, pp. 855–865 (Mar. 1989).
Holland, J.J., MaLaren, L.C., and Syverton, J.T., J. Exp. Med., 110, pp. 65–80 (1959).
Mendelsohn, C., Johnson, B., Lionetti, K., Nobis, P., Wimmer, E., and Rancaniello, V., P.N.A.S. USA, 83, pp. 7845–7849 (Oct. 1986).

*Primary Examiner*—Jacqueline M. Stone
*Assistant Examiner*—Deborah Crouch
*Attorney, Agent, or Firm*—John P. White; Albert Wai-Kit Chan

[57] ABSTRACT

The subject invention provides an isolated nucleic acid molecule which comprises nucleic acid encoding a polypeptide which has the biological activity of a receptor for poliovirus and in addition, provides a purified polypeptide which has this activity. The subject invention also provides a method for inducing the production of a polypeptides which includes the use of expression vectors in a host vector system. Therapeutic compositions comprising purified polypeptides which have the biological activity of a receptor for poliovirus are also provided for as are methods of treating and preventing human poliovirus infection. Further, the subject invention provides a method of producing a transgenic animal expressing human poliovirus receptors. The subject invention provides a method of testing the efficacy of a poliovirus receptors vaccine which comprises administering the vaccine to a transgenic animal described above and determining whether the resulting transgenic animal is protected from infection by human picornavirus. Lastly, a method of testing the virulence of a picornavirus vaccine is provided.

8 Claims, 13 Drawing Sheets

```
      1                    10                    20
      M  A  R  A  M  A  A  A  W  P  L  L  L  V  A  L  L  V  L  S  W  P  P  P  P  G
      ATGGCCCGAGCCATGGCCGCCGCCTGGCCGCTGCTGCTGGTCGCGCTGCTGGTCCTGGCCACCCCCAGGA        75
                           35                             45
      T  G  D  V  V  V  Q  A  P  T  Q  V  P  G  F  L  G  D  S  V  T  L  P  C  Y
      ACCGGGGACGTCGTGGTCCAGGCCCCCACCCAGGTGCCCGGCTTCTTGGGCGACTCCGTGACCCTGCCCTGCTAC    150
                                 60                             70
      L  Q  V  P  N  M  E  V  T  H  V  S  Q  L  T  W  A  R  H  G  E  S  G  S  M
      CTACAGGTGCCCAACATGGAGGTGACGCATGTGTCACAGCTGACTTGGGCGCGACATGGTGAATCTGGCAGCATG    225
                                 85                             95
      A  V  F  H  Q  T  Q  G  P  S  Y  S  E  S  K  R  L  E  F  V  A  A  R  L  G
      GCCGTCTTCCACCAAACGCAGGGCCCCAGCTATTCGGAGTCCAAACGGCTGGAATTCGTGGCCAGACTGGGC      300
                           110                           120
      A  E  L  R  N  A  S  L  R  M  F  G  L  R  V  E  D  E  G  N  Y  T  C  L  F
      GCGGAGCTGCGGAATGCCTCGCTGAGGATGTTCGGGCTTGCGCGTAGAGGATGAAGGCAACTACACCTGCCTGTTC    375
                                 135                           145
      V  T  F  P  Q  G  S  R  S  V  D  I  W  L  R  V  L  A  K  P  Q  N  T  A  E
      GTCACGTTCCCGCAGGGCAGGAGCGTGGATATCTGGCTCCGAGTGCTTGCCAAGCCCCAGAACACAGCTGAG      450
                                 160                           170
      V  Q  K  V  Q  L  T  G  E  P  V  P  M  A  R  C  V  S  T  G  G  R  P  P  A
      GTTCAGAAGGTCCAGCTCACTGGAGAGCCAGTGCCCATGGCCCGCTGCGTCTCCACAGGGGTGCCCCGCCAGCC    525
```

FIGURE 4B

```
      Q  I  T  W  H  S  D  L  G  G  M  P  N  T  S  Q  V  P  G  F  L  S  G  T  V
         185                          195
CAAATCACCTGGCACTCAGACCTGGGCGGGATGCCCAATACGAGCCAGGTGCCAGGGTTCCTGTCTGGCACAGTC    600
                210                          220
      T  V  T  S  L  W  I  L  V  P  S  S  Q  V  D  G  K  N  V  T  C  K  V  E  H
                    235                          245
ACTGTCACCAGCCTCTGGATATTGGTGCCCTCAAGCCAGGTGGACGGCAAGAATGTGACCTGCAAGGTGGAGCAC    675
      E  S  F  E  K  P  Q  L  L  T  V  N  L  T  V  Y  Y  P  P  E  V  S  I  S  G
                    260                          270
GAGAGCTTTGAGAAGCCTCAGCTGCTGACTGTGAACCTCACCGTGTACTACCCCCCAGAGGTATCCATCTCTGGC    750
      Y  D  N  N  W  Y  L  G  Q  N  E  A  T  L  T  C  D  A  R  S  N  P  E  P  T
                          285                          295
TATGATAACAACTGGTACCTTGGCCAGAATGAGGCCACCCTGACCTGCGATGCTCGCAGCAACCCAGAGCCCACA    825
      G  Y  N  W  S  T  M  G  P  L  P  P  F  A  V  A  Q  G  A  Q  L  L  I  R
                    310                          320
GGCTATAATTGGAGCACGATGGGTCCCCTGCCACCCTTTGCTGTGGCCCAGGGCGCCCAGCTCCTGATCCGT    900
      P  V  D  K  P  I  N  T  T  L  I  C  N  V  T  N  A  L  G  A  R  Q  A  E  L
                          335                          345
CCTGTGGACAAACCAATCAACACAACTTTAATCTGCAACGTCACCAATGCCCTAGGAGCTCGCCAGGCAGAACTG    975
      T  V  Q  V  K  E  G  P  P  S  E  H  S  G  M  S  R  N  A  I  E  L  V  L
                    360                          370
ACCGTCCAGGTCAAAGAGGGACCTCCCAGTGAGCACTCAGGCATGTCCCGTAACGCCATCATCTTCCTGGTTCTG   1050
      G  I  L  V  F  L  I  L  L  G  I  G  I  Y  F  Y  W  S  K  C  S  R  E  V  L
GGAATCCTGGTTTTTCTGATCCTGCTGGGGATCGGGATTTATTTCTATTGGTCCAAATGTTCCCGTGAGGTCCTT   1125
```

FIGURE 4C

```
      W   H   C   H   L   C   P   S   S
      TGGCACTGTCATCTGTGTCCCTCGAGT

DIVERGED COOH-TERMINI

385
H20B:  E   H   H   Q   S   C   R   N   *
       GAGCATCACCAGAGCTGCCGTAATTGA  1179

385
       T   E   H   A   S   A   S   A   N   G   H   V   S   Y   S   A   V   S   R   E   N   S   S
H20A: ACAGAGCATGCCAGCGCCTCAGCTAATGGGCATGTCTCCTATTCAGCTGTGAGCAGAGAACAGCTCT  1221
       408
       S   Q   D   P   Q   T   E   G   T   R   *
       TCCCAGGATCCACAGACAGAGGGCACAAGGTGA  1254
```

FIGURE 5

TRANSGENIC MOUSE EXPRESSING DNA SEQUENCES ENCODING THE HUMAN POLIOVIRUS RECEPTOR

This application is a continuation of U.S. Ser. No. 495,744, filed Mar. 19, 1990, now abandoned, which is a continuation-in-part of U.S. Ser. No. 321,957, now abandoned, filed Mar. 10, 1989, the contents of which are hereby incorporated by reference into the present disclosure.

BACKGROUND OF THE INVENTION

Poliovirus is a small, iscosahedral RNA-containing picornavirus best known as the etiologic agent of paralytic poliomyelitis. Infection begins when virus is ingested and replicates in the gut, leading to a viremia. In a small number of infected individuals, virus invades the central nervous system from the blood. Lytic viral replication with motor neurons in the brain and spinal cord results in destruction of these cells and the characteristic flaccid paralysis of poliomyelitis [Bodian D., Science 12:105–108 (1955)].

Although during its viremic stage many tissues are exposed to poliovirus, replication is limited to the oropharyngeal and intestinal mucosa, the Peyer's patches of the ileum, and motor neurons within the central nervous system. Several experimental results support the suggestion that the restricted tissue tropism of poliovirus is a result of limited expression of specific viral attachment sites, or receptors. In binding studies using tissue homogenate, the poliovirus receptor is detected only in tissues that are sites of poliovirus replication [Holland, J. J. Virology 15:312–326 (1961)]. Furthermore, lack of susceptibility to poliovirus infection, both in primate and non-primate cell types, can be circumvented by introducing viral RNA into the cells by transfection, indicating that resistance to infection is due to a block in binding, entry, or uncoating of poliovirions [Holland, J. J., McLaren, J. C., and Syverton, J. T., J. Exp. Med. 110:65–80 (1959)]. Finally, the results of gene transfer experiments indicated the mouse L cells transformed with human DNA express poliovirus receptors at the cell surface and become susceptible to infection [Mendelsohn, C., Johnson, B., Leonetti, K. A., Nobis, P., Wimmer, E. and Racaniello, V. R., Proc. Natl. Acad. Sci. USA 83:7845–7849 (1986)].

Work in other viral systems strongly implicates cellular receptors in tissue tropism and pathogenesis. For example, the human T cell glycoprotein CD4 is the receptor for HIV-I [Maddon, P. J., Dalgeleish, A. G., McDougal, J. S., Clapham, P. R., Weiss, R. A. and Axel, R. Cell 47:333–348 (1986)]. Expression of the CD4 on T helper cells is though to be responsible for the selective infection and destruction of these cells observed in individuals infect with HIV-I Human CD4-negative cells, which are resistant to infection by HIV-I, can be rendered susceptible to infection by transfection with CDNA clones encoding the CD4 receptor.

Biochemical studies indicated that the poliovirus receptor is an integral membrane protein [Krah, D. L. and Crowell, R. L., Virology 118:148–156 (1982)]. However, it has not been possible to purify the receptor protein from membrane preparations using assays that require binding of virus or antibody, probably due to the liability of the respective binding sites. Several monoclonal antibodies have been isolated which inhibit the binding of poliovirus to cultured cells [Minor, P. D., Pipkin, P. A., Hockley, D., Schild, G. C. and Almond, J. W. Virus Res. 1:203–212 (1984); Nobis, P., Zibirre, R., Meyer, G., Kuhne, J., Warnecke, G. and Kock, G. J. Gen. Virol. 6:2563–2569 (1985); Shepley, M. P. Sherry, B. and Weiner, H. L. Proc. Natl. Acad. Sci, USA 85:7743–7747 (1988)]. Monoclonal antibody D171 competes with the 3 poliovirus serotypes for a common high affinity binding site on permissive cells and does not bind to cells that are resistant to poliovirus infection [Nobis et al., (1985)]. HeLa cells contain approximately 100,000 D171 binding sites (P. Nobis, personal communication) and 3000 poliovirus binding sites [Lonberg-Holm, K. and Philipson, L. Receptors and Recognition. (Chapman and Hall, London) (1981)], suggesting that virus binding is multivalent. A second type of monoclonal antibody partially blocks infection with poliovirus type 2 and to a lesser extent with poliovirus type 1, but has little effect on type 3 binding [Shepley et al., (1988)]. This antibody recognizes a 100 kd protein in the membrane of poliovirus-susceptible cell lines and human spinal cord, and specifically stains neurons at the neuromuscular junction.

The subject invention discloses isolated genomic and CDNA clones encoding poliovirus receptors from HeLa cells. Transformation of resistant mouse cells with either of two CDNA clones leads to expression of the receptor on the cell surface and susceptibility to poliovirus infection. Northern hybridization analysis indicates that a 3.3 kb receptor transcript is present in many human tissues, including kidney, which does not contain poliovirus binding activity and which is not a site of poliovirus replication. Thus, at least in the kidney, expression of poliovirus receptor RNA is not sufficient to permit viral infection.

The poliovirus receptor CDNA clones encode putative polypeptides of 43,000 and 45,000 daltons that contain identical extracellular and transmembrane domains, but differ at the cytoplasmic tails. Protein homology comparisons revealed that the poliovirus receptor is a new member of the immunoglobulin superfamily [For a review of the immunoglobulin superfamily see: Williams, A. F., and Barclay A. N. Ann. Rev. Immunol, 6:381–405 (1988)]. The extracellular portion of the receptor may be folded into a structure composed of 3 domains stabilized by intrachain disulfide bonds.

SUMMARY OF THE INVENTION

The subject invention provides an isolated nucleic acid molecule encoding a polypeptide which is a naturally occurring receptor for picornavirus.

In addition, the subject invention provides a purified polypeptide which has the binding activity of a receptor for picornavirus.

The subject invention also provides a method for inducing the production of a polypeptide which includes the use of expression vectors in a host vector system. Therapeutic compositions comprising purified polypeptides which have the binding activity of a receptor for picornavirus are also provided for as are methods of treating and preventing human poliovirus infection.

Further, the subject invention provides a method of producing a transgenic animal expressing human picornavirus. This comprises introducing DNA encoding the picornavirus into a fertilized egg recovered from an animal of the female sex; transferring the resulting egg to the oviduct of a pseudopregnant animal under conditions such that the female animal becomes pregnant with the egg. The animal is then treated under conditions such that the female gives birth to a litter; then selecting from the litter animals which express and have stably incorporated DNA encoding human picornavirus receptor.

Additionally, the subject invention provides a method of testing the efficacy of a picornavirus vaccine which comprises administering the vaccine to a transgenic animal described above and determining whether the resulting transgenic animal is protected from infection by human picornavirus.

Lastly, the subject invention provides a method of testing the virulence of a picornavirus vaccine to a transgenic animal described above and determining the physiological effect of the vaccine on the animal.

BRIEF DESCRIPTION OF THE FIGURES

FIGS. 1(A–B). Analysis of receptor DNA in transformants and in recombinant bacteriophages.

A) Southern blot hybridization analysis of secondary L cell transformants expressing the poliovirus receptor. Ten micrograms of genomic DNAs were digested with restriction endonuclease Bam HI, fractioned in 0.8% agarose gels, transferred to nitrocellulose and hybridized with $^{32}$P-labeled RNA SP6 transcripts from the human Alu clone blur-8 [Jelinek et al., (1980)]. Secondary transformant cell lines CM-1.1, CM-1.9, CM-1.17, CM-1.24 and CM-1.27 were derived from the primary transformant CM-1. The positions of the markers were determined by the coelectrophoresis of lambda DNA digested with Hind III. The sizes of the markers are given in kilobase pairs.

B) Restriction map of receptor genomic clones λPVR-2, λXPVR-3, and λPVR-4. Solid lines indicate human sequences and stippled lines indicate mouse sequences. The locations of Bam HI restriction sites are shown. The 10 kb and 6 kb fragments in λPVR-2 correspond to the 10 kb and 6 kb Alu-containing BamH I fragments shared among poliovirus receptor expressing secondary transformants (see FIG. 1A). The cloning site and arms of the replacement vector λ2001 are not shown. The order of the BamH I fragments in λPVR-2 was determined by gel electrophoresis of partial digestion products annealed to $^{32}$P-labeled oligonucleotide probes complimentary to the left and right cohesive ends of lambda DNA (Collaborative Research, Inc.)

FIGS. 2(A–C). Northern Hybridization analysis.

A) Total cell RNA prepared from poliovirus resistant Ltk$^-$ cells and poliovirus susceptible cell lines including HeLa cells, secondary L cell transformant CM-1.9 and human neuroblastoma SY5Y. The DNA probe is the 1 kb BamH I genomic fragment isolated from λPVR-2 (FIG. 1B).

B) Total cell RNA prepared from transformants expressing poliovirus receptor CDNA clones PSVL-H20A and PSVL-H20B. Also shown is total HeLa cell RNA and RNA from Ltk$^-$ cells transformed with herring sperm DNA. The DNA probe used is the 0.97 kb EcoR I CDNA fragment.

C) Oligo d(T)-selected RNA from HeLa cells, secondary transformant CM-1.9 and Ltk$^-$ cells. The DNA probe used is the 0.97 kb EcoR I CDNA fragment. Positions of 28S and 18S RNA markers are shown in all panels.

FIG. 3. Restriction maps of poliovirus receptor CDNA clones. The positions of EcoR I, Xho I, Sma I and Bgl II sites are shown for four CDNA clones isolated from HeLa cell CDNA libraries. Sizes of CDNA clones are: HeLa 1.7, 1,666 bp; HeLa 1.5, 1,446 bp; H20A, 2,930 bp plus a 0.45 kb 3'-EcoR I fragment whose nucleotide sequence was not determined; H20B, 2,957 bp. Clones H20B and HeLa 1.7 contain identical sequences at the respective 3' ends which are designated by open bars. Clone H20A contains unique 3' end sequences to the right of the Xho I site, drawn as a crosshatched box. Clones H20A and H20B are identical from the 5' EcoRI site to the Xho I site; however the 5' EcoR I fragment of H20A contains a deletion of 37 nucleotides 20 bp from the 5-end. The first 5'-500 bp of HeLa 1.5 CDNA, which is designated by a dotted bar, does not share sequence homology with the other CDNA clones; the sequence dissimilarity extends slightly past the EcoR I site. The sizes of the predicted proteins encoded by the poliovirus receptor CDNAS are given in daltons. DNA fragments used as hybridization probes in the studies are identified.

FIGS. 4A–4C. Nucleotide sequence and predicted acid sequence of receptor CDNAS H20A and H20B. 5'- and 3'-noncoding sequences are not shown. Nucleotides are numbered at the right margin, beginning with the first in frame ATG. Amino acids are numbered above the sequence. The signal sequence (amino acid 1-20) and transmembrane domain (amino acid 433-367) are boxed. Potential sites for N-linked glycosylation are underlined. Below are the diverged carboxy-terminal sequences of H20A and H20B, beginning at nucleotide 1153.

Figure 5:
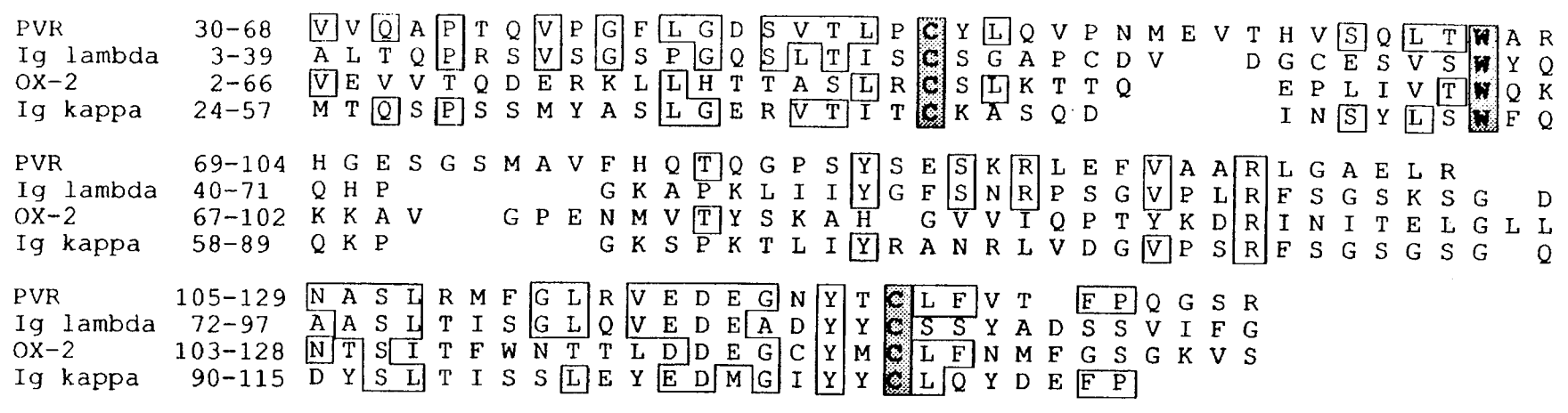

FIG. 5. Amino acid homology of poliovirus receptor domain 1 with 1g superfamily members. Identical amino acids are boxed, and conserved cysteines and tryptophan residues are shaded. IgG lambda is the Ig lambda chain V-II region, human Nig-58 [Takayasu et al., (1981)]. OX-2 is rat membrane glycoprotein precursor OX-2 [McCaughan et al., (1987)]. Ig kappa is mouse L6 Ig kappa chain V region [Pech et al., (1981)]. Homologies were detected by searching the NBRF protein database with the FASTP program [Dayhoff et al., (1983)] which was run with a bias and break penalty of 6. 120 random runs were performed.

FIG. 6. Structure of poliovirus receptor polypeptide. The domain structure of the poliovirus receptor is based on the deduced amino acid sequence. The 3 cysteine pairs are shown as well as the number of amino acids between each cysteine pair and between the loops. The transmembrane domain is designated by a stippled bar. The lengths of the diverged COOH-terminal cytoplasmic domains of H20A and H20B are given in amino acid residues.

FIG. 7. Poliovirus receptor transcripts in human tissues and cell lines. Total RNAs from human tissues and cell lines were analyzed by Northern hybridization; the DNA probed employed is the 0.4 kb Sma 1-Eco RI fragment of H20B (FIG. 3). Human tissue samples were obtained post-operatively or post mortem and showed no evidence of degradation as judged by the rations and abundance of 28S and 18S ribosomal RNAs. The B-lymphocyte RNA was isolated from the J558 plasmacytoma line, and the T cell RNA from the Jurkat T cell line. Macrophages were purified from human blood as described [Horowitz and Silverstein, (1980)]. Positions of 28S and 18S RNA markers are shown.

FIG. 8. Restriction map of DNA inserts from cosmid clones PRG-1 and PRG-3 containing the PVR gene. Sites for restriction endonuclease BamHI (B) are indicated. Sequences homologous to the protein coding region of PVR CDNA clones H20A and H20B (Mendelsohn et al. 1989) are shown, as determined by Southern blot hybridization analysis of the cosmid DNAs.

FIG. 9. Poliovirus binding assay of transgenic and non-transgenic mouse tissue homogenates. Homogenates of different mouse tissues were mixed with poliovirus type Mahoney, incubated 2 hr at room temperature, and infectious virus was determined by plaque assay on HeLa cell monolayers. Percent binding was calculated as 100-(virus titer after incubation with homogenate/virus titer after incubation with PBS X 100).

FIGS. 10A–10C. Infection of mice with poliovirus type Mahoney. Eight transgenic F1 mice of the PRG-1-17 line and eight nontransgenic mice were inoculated intracerebrally with $1 \times 10^5$ pfu of type Mahoney poliovirus. Beginning the day of inoculation and each day thereafter, one mice was sacrificed, the brain and spinal cord was removed and homogenized in PBS, and the virus content of the tissues was determined by plaque assay on HeLa cells. Mice were also scored for paralytic disease before sacrifice. On day 3 and 5 two transgenic mice were paralyzed; these were both sacrificed and the titer of virus in brain and spinal cord separately determined; the graph shows the average of the values for the two mice. FIG. 10A, total mice paralyzed versus time; FIG. 10B, titer of virus per mg of brain; FIG. 10C, titer of virus per mg of spinal cord. Curves for transgenic and nontransgenic mice are shown.

DETAILED DESCRIPTION OF THE INVENTION

Figure 1A:
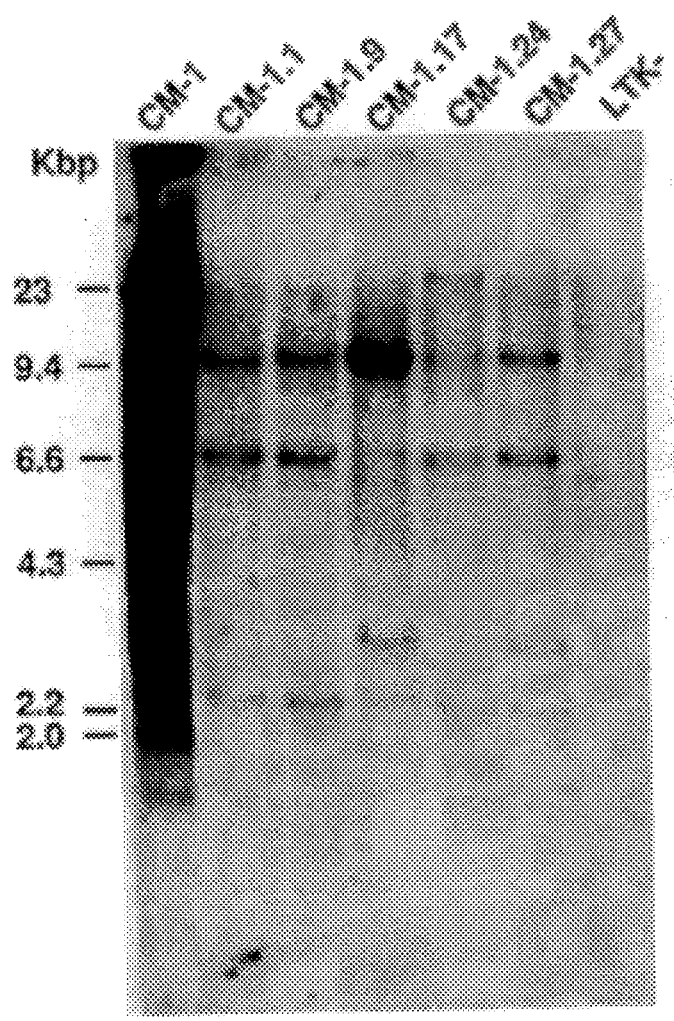
Figure 1B:
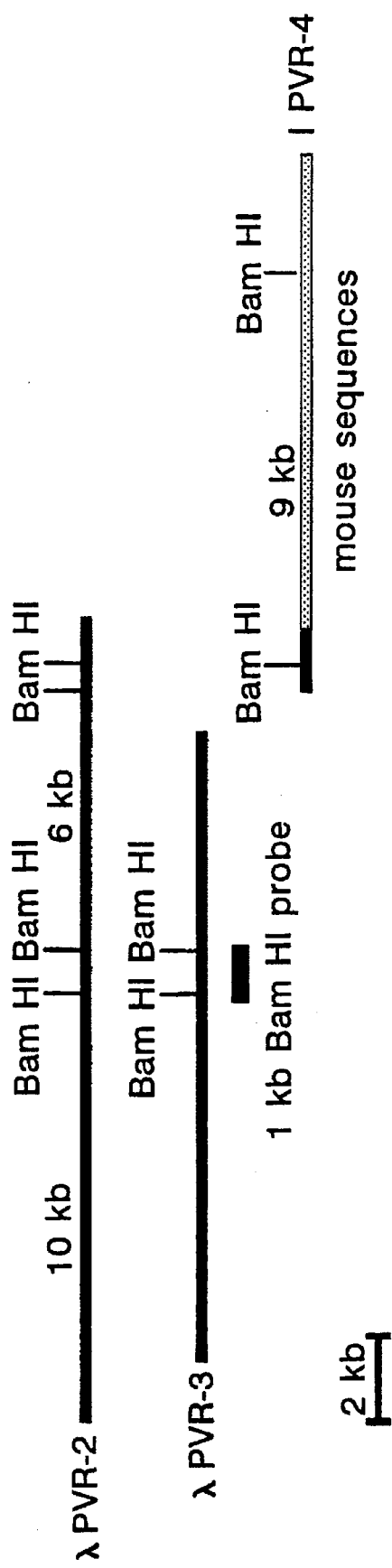
Figure 2A:
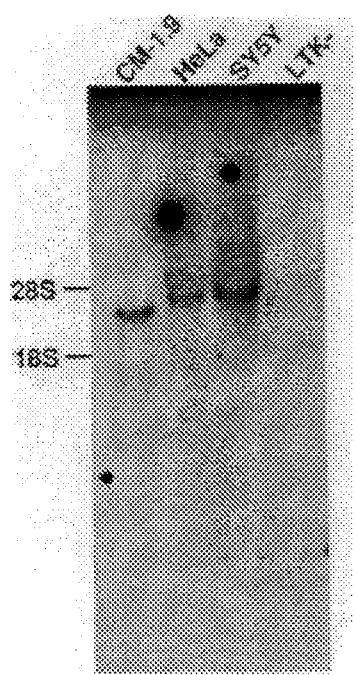
Figure 2B:
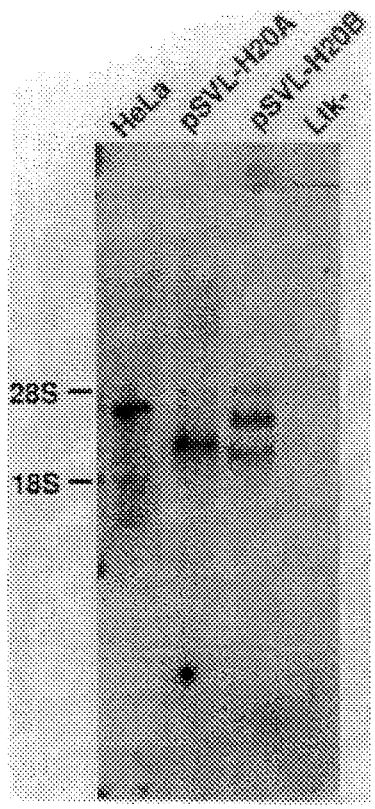
Figure 2C:
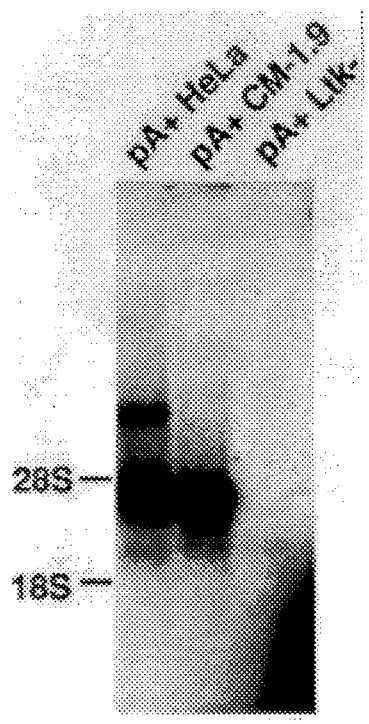

The subject invention provides an isolated nucleic acid molecule encoding a polypeptide which is a naturally occurring receptor for a picornavirus. Picornaviruses include rhinovirus, coxsackie virus, echovirus and a human poliovirus among others. Human poliovirus, a small, iscosahedral RNA-containing picornavirus is of particular interest to this invention. Nucleic acid is to include both RNA and DNA with DNA and CDNA being the nucleic acid in the preferred embodiment. The most preferred CDNA molecules being those designated H20A and H20B which have the nucleotide sequences shown in FIGS. 4A–4C. The subject invention also provides a phage expression vector or cosmid which comprises a nucleic acid encoding a polypeptide which has the biological activity of a receptor for a picornavirus. Examples of cosmids which include a nucleic acid molecule encoding a polypeptide which has the biological activity of a receptor for picornavirus include, but are not limited to the cosmids designated PRG-1 and PRG-3. PRG-1 and PRG-3 were deposited with the American Type Culture Collection (ATCC) 12301 Parklawn Drive, Rockville, Md., U.S.A. on Mar. 9, 1990 and accorded ATCC Accession Nos. 68252 and 68253, respectively. The deposits were made pursuant to the Budapest Treaty for the International Recognition of the Deposit of Microorganisms for the Purposes of Patent Procedure (Budapest Treaty). The subject invention also provides for the RNA and polypeptides which are encoded by PRG-1 and RRG-3, and any fragment thereof. The subject invention further provides for the use of a genomic DNA molecule.

An isolated nucleic acid molecule encoding a soluble polypeptide capable of binding to a picornavirus is also provided for, as is the soluble polypeptide encoded by this nucleic acid. This nucleic acid molecule is especially useful when the picornavirus comprises a human poliovirus. The soluble polypeptide encoded by this nucleic acid is also a product of this invention.

A purified polypeptide which has the binding activity of a receptor for a picornavirus is also disclosed by the subject invention. This purified polypeptide may be produced by any of the methods disclosed in the invention. In the preferred embodiment, the purified polypeptide comprises a purified polypeptide which has the binding activity of a receptor for a human poliovirus. A purified peptide encoded for by the nucleic acid molecule as described above is also provided. This polypeptide has the binding activity of a receptor for a picornavirus.

Additionally, the subject invention discloses a purified polypeptide encoded by the CDNA molecule H20A and is characterized by a calculated molecular weight of 45,000. A purified polypeptide encoded by the CDNA molecule H20B is characterized by a calculated molecular weight of 43,000.

This invention further provides for expression vectors which comprise a nucleic acid encoding any of the above-identified polypeptides. These expression vectors include but are not limited to: 1) an expression vector which comprises nucleic acid encoding a polypeptide which is a naturally occurring receptor for a picornavirus; 2) an expression vector which comprises nucleic acid encoding a purified polypeptide which has the binding activity of a receptor for a human poliovirus; 3) an expression vector which comprises a nucleic acid encoding a purified polypeptide encoded by the CDNA molecule H20A, characterized by a calculated molecular weight of about 45,000 daltons; 4) an expression vector which comprises nucleic acid encoding a purified polypeptide encoded by the CDNA molecule H20B, characterized by a calculated molecular weight of about 43,000; 5) an expression vector which comprises a nucleic acid encoding a soluble polypeptide which has the biological activity of a receptor for a picornavirus; and 6) an expression vector which comprises a nucleic acid encoding a soluble polypeptide which has the biological activity of a receptor for human poliovirus. The above-identified expression vectors, include but are not limited to: plasmid expression vectors, phage expression vectors, yeast expression vectors, viral expression vectors, mammalian expression vectors or any variant thereof, as provided for in the subject invention.

The subject invention also provides for a host vector system which comprises a suitable host and an expression vector as described above. A host vector system comprises: 1) a suitable bacterial cell and an plasmid or phage expression vector; 2) a suitable yeast cell and a yeast expression vector; 3) a suitable eucaryotic cell and a viral expression vector; and 4) a suitable mammalian cell and a mammalian expression vector.

The subject invention further provides a method of producing a polypeptide which comprises culturing or growing the host vector systems previously described under conditions such that the polypeptide is produced and recovering the polypeptide. The method of producing an expression vector and choosing an appropriate host vector system is known to one skilled in the art. The novelty of the present methods is in the use of previously unknown nucleic acids to effect the production of polypeptides which bind to picornaviruses. Accordingly, a detailed description of known methods is not included in this section. However, specific material may be found in the Experimental Detail Section.

The subject invention further provides a therapeutic composition which comprises a therapeutically effective amount of one of the above-identified polypeptides and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water emulsion, and various types of wetting agents. The polypeptides include but are not limited to: 1) a purified polypeptide which has the binding activity of a receptor for a picornavirus; 2) a purified polypeptide which has the binding activity of a receptor for a human poliovirus; 3) a purified polypeptide encoded for by the CDNA molecule designated H20A having the nucleotide sequence shown in FIGS. 4A–4C characterized by a calculated molecular weight of 45,000; 4) polypeptide encoded for by the CDNA molecule designated H20B having the nucleotide sequence shown in FIGS. 4A–4C characterized by a calculated molecular weight of 43,000; 5) a soluble polypeptide capable of binding to a picornavirus; and 6) a soluble polypeptide encoded by the nucleic acid encoding a polypeptide which is a naturally occurring receptor for a human poliovirus. The pharmaceutically acceptable carrier encompasses any of the standard pharmaceutical carriers such as sterile solution, tablets, coated tablets and capsules. Typically such carriers contain excipients such as starch, milk, sugar, certain types of clay, gelatin, steric acid, talc, vegetable fats or oils, gums, glycols or other known excipients. Such carriers may also include flavor and color additives or other ingredients. Compositions comprising such carriers are formulated by well known conventional methods. However, the compositions comprising the subject polypeptides are unknown.

Also provided for in the subject invention is an antibody directed to any of polypeptides described above. These antibodies may be produced by any the methods known in the art. Antibodies are to include IgG, IgA, IgD, IgA, IgM, and antibody fragments such as $F(ab')_2$ and Fab.

A therapeutic composition which comprises an amount of an antibody directed to the above-identified polypeptides to which a therapeutically effective amount of a drug is bound and a pharmaceutically acceptable carrier is also provided for.

The antibodies may also be labelled with a detectable marker. These may include but are not limited to markers which are radioactive, radioopaque, paramagnetic or a metal. These labelled antibodies may be used for imaging areas of the body containing picornavirus receptors and may be detected by x-ray or MRI imaging techniques known to those skilled in the art.

The disclosed polypeptides of the subject invention may also be labeled with a detectable marker. These labelled polypeptides may then be used in much the same manner as the labelled antibodies to bind to cells expressing the picornavirus receptor. Again, the labels may include those which are radioactive, radioopaque, paramagnetic or a metal.

A further provision of the subject invention is a therapeutant comprising a fragment of a human poliovirus particle capable of binding to the purified polypeptide which has the binding activity of receptor for human poliovirus and a drug which is attached to the poliovirus particle. In the preferred embodiment, the drug is covalently attached. A therapeutically effective amount of the therapeutant described above and a pharmaceutically acceptable carrier is provided. Pharmaceutically acceptable carriers are discussed hereinabove.

The two described therapeutic compositions may be used to increase the concentration of a drug in the vicinity of cells having receptors for picornavirus or specifically human poliovirus. The subject invention provides a method of delivering a drug which comprises administering to a subject a therapeutic composition, either comprising an amount of: 1) antibody directed to a polypeptide which has the biological activity of a receptor for a picornavirus; or 2) a fragment of a human poliovirus particle capable of binding to the polypeptide which has the biological activity of a receptor for human poliovirus. The method of administering may be any of the standard methods including but not limited to oral, intravenous, intraperitoneal, intramuscular or subcutaneous. The exact form of administration will vary depending on the effect desired and the attendant circumstances. However, one skilled in the art will readily be able to determine which form of administration is most appropriate and what dosage is required.

The subject method provides a method of preventing in a subject human poliovirus infection which comprises administering to a subject a prophylactically effective amount of one of the polypeptides which has the biological activity to bind human poliovirus. In the preferred embodiment the polypeptide is a soluble polypeptide encoded by a nucleic acid molecule encoding a soluble polypeptide capable of binding to a picornavirus, most preferably human poliovirus.

The subject invention also provides a method of treating a patient afflicted with a human poliovirus infection which comprises administering to the patient a therapeutic composition which comprises a therapeutically effective amount of one of the polypeptides capable of binding to a picornavirus.

Both the method of preventing human poliovirus infection and the method of treating a patient afflicted with human poliovirus infection are particularly suited for use with infants and their parents. In this manner it may be used after vaccination and as a supplement to existing oral vaccinations. Also, by providing a direct method of "typing up" human poliovirus, a therapy may be offered to patients who are immunosuppressed in their immunity to human poliovirus.

The subject invention provides a transgenic animal having the DNA which encodes a polypeptides which has the biological activity of a receptor for a picornavirus stably integrated into the chromosomal DNA of the animal. This DNA may include but is not limited to: 1) CDNA; 2) CDNA designated H20A having the nucleotide sequence shown in FIGS. 4A–4C; 3) CDNA designated H20B having the nucleotide sequence shown in FIG. 4; 5) cosmid DNA designated PRG-1; 6) cosmid DNA designated PRG-3); and 7) genomic DNA. In the preferred embodiment the animal is a mouse.

A method of producing a transgenic animal expressing human picornavirus receptor is also provided. This method comprises: 1) introducing DNA encoding the picornavirus receptor into a fertilized egg recovered from an animal of the female sex; 2) transferring the resulting egg to the oviduct of a pseudopregnant animal under conditions such that the female animal becomes pregnant with the egg; 3) treating the resulting pregnant female such that the female gives birth to a litter; and 4) selecting from the litter animals which express and have stably incorporated DNA encoding human picornavirus receptor. The steps are briefly: 1) recovering eggs from the oviducts of pregnant female animals; 2) microinjecting the DNA which preferably contains a promoter sequence into the male pronucleus; 3) transferring the eggs to pseudopregnant female animal; and 4) removing tissue from the offspring to determine DNA incorporation by standard methods. The technical aspects of this method is detailed in the Experimental Detail section under Production of Transgenic Mice Expressing a Poliovirus Receptor. In the preferred embodiment the picornavirus is human poliovirus and the transgenic animal is a mouse.

A method of testing the efficiency of a picornavirus vaccine is also provided. This method comprises administering the vaccine to a transgenic animal which has the DNA encoding for a polypeptide which binds to picornavirus, stably integrated into its chromosomal DNA and determining whether the resulting transgenic animal is protected from infection by human picornavirus. Protection of the transgenic animal may be determined by various physiological tests including but not limited to determining the levels of virus in serum, spinal fluid or organs; observing damage to organs caused by the virus; and observing gross motor dysfunction caused by the virus. In the preferred embodiment the picornavirus is human poliovirus and the transgenic animal is a mouse.

Lastly, the subject invention provides a method of testing the virulence of a picornavirus vaccine which comprises administering the vaccine to a transgenic animal as above-described and determining the physiological effect of the vaccine on the animal. This method provides an economical means for testing poliovirus vaccine, as well as other picornavirus vaccines. Currently, primates must be used to test the virulence of the currently used vaccines. This is because human poliovirus will only effect animals which have receptors for human poliovirus.

The subject invention provides a transgenic animal having DNA which encodes for a polypeptide which has the biological activity of a receptor for picornavirus and particularly human poliovirus. By allowing a vaccine to be tested without using expensive and limited primates, the subject invention provides a clear advantage over the prior art. The method for testing human poliovirus vaccine requires primates to be sacrificed and neurological tissue to be histologically examined to determine the extent of damage caused by various levels of the vaccine. In the preferred embodiment where the transgenic animal is a mouse and the physiological effect determined is neurological damage, a low cost readily repeatable method of testing virulence of a human poliovirus is obtained using technologies currently employed in the primate system.

EXPERIMENTAL DETAILS

Cells, Virus and Antibodies

HeLa S3 cells were grown in suspension culture or monolayer as described [La Monica, N., Meriam, C. and Racaniello, V. R. J. Virol. 57:515–525 (1986)]. $Ltk^-aprt^-$ fibroblasts were maintained in Dulbecco's modified Eagle's medium (DMEM) containing 10% calf serum, 100 μg of penicillin per ml, 100 μg streptomycin per ml, 20 μg bromodeoxyuridine per ml, and 50 μg of diaminopurine per ml. $Ltk^-aprt^-$ cells were subcultured in the same medium without bromodeoxyuridine and diaminopurine 48 hr prior to DNA transformation. Primary and secondary poliovirus-sensitive transformants were grown in DMEM medium containing 10% fetal bovine serum, 100 Mm hypoxanthine/0.4 mM aminopterin/16 Mm thymidine (HAT). Poliovirus strains used were type 1 Mahoney, type 2 Lansing and type 3 Leon. The mouse monoclonal antibody D171 directed against the human poliovirus receptor was a generous gift of P. Nobis [Nobis et al., (1985)].

DNA Transformation $Ltk^-aprt^-$ cells ($7.5 \times 10^5$) that had been cultured without drugs for 48 hr were seeded in 10-cm plastic cell culture plates 12 hr before use. Each plate was treated with 1 ml of a DNA-calcium phosphate coprecipitate consisting of 25 μg of high molecular weight DNA and 1 μg of a plasmid containing the herpesvirus thymidine kinase gene prepared as described [Graham, F. and van der Eb, J. Virol 52:456–457 (1973); Wiglet, M., Pellicer, A., Silverstein, S., Axel. R. Cell 14:725–731 (1978)]. After 16 hr of incubation at 37° C. the medium was replaced and incubation was continued for an additional 24 hr prior to addition of HAT medium. After 2 weeks of growth in HAT medium, each plate contained 1000–5000 $tk^+$ colonies.

Virus Infection

To identify poliovirus-sensitive L cell transformants, monolayers of $LtK^+$ cells were subcultured 1:2, and one plate was infected with poliovirus type 1 Mahoney at a multiplicity of infection of 0.1. After adsorption, the plates were washed 3 times to remove unattached virus and the medium was replaced. Aliquots of supernatants were removed at different times after infection and virus titers were determined by plague assay on HeLa cell monolayers [La Monica et al., (1986)].

Rosetting and Planning

Transformants that express poliovirus receptors were visualized on plates of $tk^+$ transformants using an in situ rosette assay [Littman, D., Thomas, Y., Maddon, P., Chess, L. and Axel, R. Cell 40:237–246 (1985)]. Cell monolayers were first treated with 1.25 μg per ml of monoclonal antireceptor antibody D171 followed by human erythrocytes coated with goat anti-mouse IgG antibody. Cells expressing the poliovirus receptor became covered with erythrocytes and could be located, removed from plates with cloning cylinders, and grown into large cultures. Cell cultures were enriched for poliovirus receptor-positive cells using a panning technique as described [Mendelsohn et al., (1986)].

RNA and DNA Isolation

Total RNA was isolated from cultured cells and tissues by homogenization in 4M guanidine issothiocyanate followed by centrifugation on a cushion of CsC1 [Chirgwin J., Przybyla, A., MacDonald, R. and Rutter W. Biochem. 18:5294–5299 (1979)]. Poly A+ RNA was selected by chromatography on prepacked oligo d(T) cellulose columns (Collaborative Research) according to the method of the manufacturer. Genomic DNA was prepared from cultured cells as described [Mendelsohn et al. (1986)].

Northern and Southern Hybridization

RNA was fractioned on 1% agarose formaldehyde gels [Goldberg, D. Proc. Natl. Acad. Sci. USA 77:5794–5799 (1980)] and transferred to either Zeta-Probe (Bio-Rad) or nitrocellulose (Schleicher & Schuell) membranes. For Southern hybridization, genomic DNA was digested with restriction endonucleases (4 units/μg) under conditions recommended by New England Biolabs, and fractionated on 0.8% agarose gels. DNA was transferred to nitrocellulose filters according to the method of Southern [Southern, E. M. J. Mol. Biol. 98:503–517 (1975)]. Conditions for hybridization of nitrocellulose filters with DNA probes were as described (Schleicher and Schuell). The conditions for hybridization of nitrocellulose filters with RNA probes were as described [Melton, D., Krieg, P., Rebagliati, M., Maniatis, T., Zinn, K. and Green, M. Nucleic Acids Res. 12:7035–7056 (1984)]. After hybridization, both Southern and Northern blots were washed 3 times at room temperature then once at 65° C. in 0.3M NaCl/0.03M sodium citrate, pH 7.0 containing either 0.5% $NaDodSO_4$ (for nitrocellulose filters) or 1% $NaDodSO_4$ (for Zeta-Probe membranes). $^{32}$-P labeled DNA probes were prepared with the oligolabelling kit (Pharmacia). Southern hybridization with the human Alu repeat blur-8 was performed with RNA probes synthesized in vitro with SP6 polymerase [Melton et al., (1984)].

Construction of Genomic Libraries

Genomic Libraries were constructed according to Maniatis [Maniatis, T., Fritsch, E. and Sambrook, J. Molecular Cloning: A Laboratory Manual. Cold Spring Harbor Laboratory, Cold Spring Harbor, N.Y. (1982)], 300 μg of high molecular weight genomic DNA prepared from CM-1.24 L-cell transformants was partially digested with 36 units of Sau 3A (New England Biolabs) and fractionated on a 10–40% sucrose gradient. Fractions containing fragments ranging in size from 15–20 kb were pooled, ligated to λ2001 arms which were predigested with BamH I and Hind III (Stratgene), and packaged using Gigapack Gold extracts (Stratagene). Libraries were plated on *E. coli* P2392 and screened in duplicate with the blur-8 RNA probe [Jelinek, W., Toomey, P., Leinwand, L., Duncan, C., Biro, P., Choudary, P., Weissman, S., Rubin, C., Houck, C., Deininger, P. and Schmid, C. Proc. Natl. Acad. Sci. USA 77:1398–1402 (1980) using the hybridization and wash conditions described for southern blots.

CDNA Libraries

CDNA was synthesized from Hela cell poly (A)+ RNA purified by two cycles of oligo d(T) cellulose chromatography. First strands of CDNA were synthesized using Moloney murine leukemia virus reverse transcriptase (Bethesda Research Laboratories) according to the conditions supplied by the manufacturer. Second strands of CDNA were synthesized using the procedure of Gubler and Hoffman [Gubler, U. and Hoffman, B. Gene 25:263–269 (1983)]. Following second strand synthesis, double stranded CDNAS were treated with T4 DNA polymerase (New England Biolabs) and ligated to EcoR I adapters (Pharmacia). The adapter-containing CDNA was phosphorylated using T4 polynucleotide kinase (Boehringer Mannheim) and fractionated on Sepharose CL-6B spin columns (5'-3', Inc.) to remove small CDNA products and unligated EcoR I adapters. The double stranded CDNA was ligated to EcoR I-digested λgt10 arms (Stratagene), and packaged using Gigapack Gold extracts (Stratagene). An unamplified CDNA library containing $1.2 \times 10^6$ recombinants was plated on *E. coli* C600Hf1-. Duplicate filters were hybridized with DNA probes prepared by the oligolabelling method, using hybridization and washing conditions described for Northern and Southern blots.

CDNA clones HeLa 1.5 and HeLa 1.7 were obtained by screening a HeLa cell CDNA library constructed in gt11 (Stratgene, Inc.) with the 1 kb BamH I genomic probe. H20A and H20B were obtained by screening the HeLa CDNA library described above with the 0.97 kb EcoR I DNA probe from HeLa 1.5.

Expression of Receptor CDNA Clones

A 1.8 Sma I-Bgl II fragment from H20A was subcloned expression vector PSVL (Phamarcia) at the Sma I and Bam HI cloning sites, producing PSVL-H20A. PSVL-H20B was constructed in a similar way using a 2.3 kb Sma I-Bgl II fragment. Both constructs contain the entire coding sequence of the poliovirus receptor. To determine whether these CDNAS encoded functional receptors, L cells were transformed with $CaPO_4$ precipitates containing either PSVL-H20A, PSVL-H20B, or herring sperm DNA, as described above. Transformed cells were assayed for susceptibility to poliovirus infection as described above. Stable Ltk$^+$ cell lines expressing functional poliovirus receptors were isolated as described above.

DNA Sequencing

Restriction fragments derived from cloned CDNA inserts subcloned into M13 vectors [Yanisch-Peron, C., Vieira, J. and Messing, J. Gene 33:103–119 (1985)], and the nucleotide sequence was determined by the dideoxy method [Sanger, F., Nicklen, S. and Coulson, A. Proc. Natl. Acad. Sci. USA 74:5463–5467 (1977)]. In some cases nested deletions were constructed using the Exo-Mung system (Stratagene) or the Cyclone system (International Biotechnologies, Inc.).

Isolation of Cosmid Clones Containing the Gene Encoding the Cell Receptor for Poliovirus (PVR)

Figure 8:
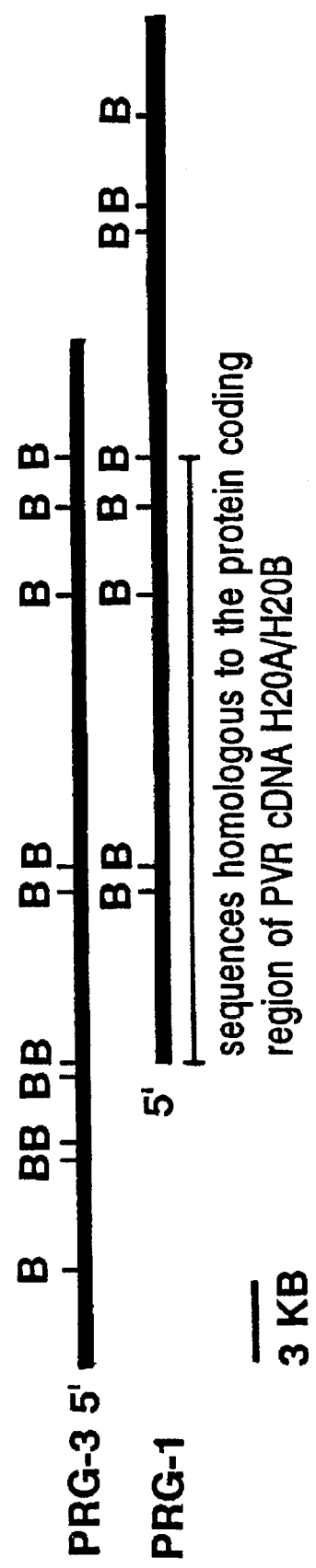

Genomic DNA was prepared from HeLa cells as described (Mendelsohn et al., Cellular Receptor for Poliovirus: Nucleotide Sequence and Expression of a New Member of the Immunoglobulin Superfamily, Cell, 56:855–865 (1989) and partially digested with restriction endonuclease MboI. The digested DNA was fractionated by electrophoresis on low melting agarose gels. DNAs in the size range of 36–48 kb were excised from the gel, and the agarose was melted and the DNA purified by phenol extraction and ethanol precipitation. The DNAs were ligated to the cosmid vector pWE15 (Stratagene) that had been digested with BamHI. The ligation mixtures were packaged into bacteriophage lambda heads (Gigapack Gold, Stratagene) and plated on *E. coli* NM554 under kanamycin selection. Resulting colonies were screened for PVR gene insert by colony hybridization (Maniatis et al., 1982), using DNA probes derived from PVR CDNAS (Mendelsohn et al., 1989). A total of $1.1 \times 10^6$ colonies were screened, and six positively hybridizing clones were obtained. Two cosmid clones, called PRG-1 and PRG-3, were selected for further analysis. Restriction maps of these cosmid clones are shown in FIG. 8. The DNA insert of PRG-1 is 37 kb in length and that of PRG-3 in 36 kb. Southern analysis with cloned PVR CDNA (Mendelsohn et al., 1989) revealed that both cosmid clones contained the PVR coding region. In addition, PRG-3 extended in the 5'-direction more than PRG-1, while PRG-1 extended more 3' than PRG-3.

Cosmid Clones PRG-1 and PRG-3 Encode Functional PVR

To determine whether cosmid clones PRG-1 and PRG-3 encode functional PVR, the cosmid DNAs were transformed into cultured mouse L cells, and 48 hr later the cells were infected with poliovirus as described (Mendelsohn et al., 1989). Samples of the cell culture medium were taken at 0 and 24 hr after virus infection. The results (Table 2) indicate that both cosmids encode functional cell receptors for poliovirus, as shown by the presence of virus in the cell culture medium 24 hr post-infection. Stable L cell transformants expressing either cosmid clone were also established as described (Mendelsohn et al., 1989). Both cosmid clones gave rise to L cell transformants expressing PVR, as judged by susceptibility to poliovirus infection. Poliovirus-susceptible L clones were obtained at a high frequency (75%), indicating that the cosmid clones contain PVR promoter sequences.

TABLE 2

| COSMID | t = 0 | t = 24 |
| --- | --- | --- |
| PWE15 | 120 | 180 |
| PSVL-H20A | 80 | $4.3 \times 10^4$ |
| PRG-1 | 90 | $2.4 \times 10^4$ |
| PRG-1 | 80 | $4.3 \times 10^4$ |
| PRG-3 | 30 | $7.1 \times 10^3$ |
| PRG-3 | 110 | $4.6 \times 10^3$ |

Production of Transgenic Mice Expressing a Poliovirus Receptor

A DNA fragment containing the human poliovirus receptor gene, including promoter sequences, may be exercised from vector sequences using an appropriate restriction endonuclease, and purified by electrophoresis in low-melt agarose. The bond containing the DNA fragment may be cut out, the agarose melted and the DNA purified by phenol extraction and ethanol precipitation. Ten to twenty micrograms of the DNA may then be centrifuged to equilibrium in a CsCl gradient, and the fraction containing the DNA dialyzed for 2–3 days against 10 mM Tris Ph 7.4, 0.2 Mm EDTA, and stored at −20 degrees C.

Fertilized eggs are recoverable from female mice that have mated the previous night by dissecting the oviducts of the pregnant females. The eggs may be recovered and stored in medium M2 [Hogan, B., Constantini, F. and Lacy, E. "Manipulating the Mouse Embryo: A Laboratory Manual" Cold Spring Harbor Laboratory, Cold Spring Harbor, (1986)]. Microinjection needles are prepared from capillary tubing (Clark Electromedical Instruments, cat number GC100TF-15) on an automatic pipet puller (David Kopf, Model 700C). The microinjection needles may be filled with the DNA solution, and attached to a Leitz instrument tube, connected to a pressure injection device [Hogan et al., (1986)]. The instrument tube may in turn be connected to Leitz micromanipulator, to finely control its movement. The eggs may be placed in a depression slide containing medium M2, and viewed under a Nikon Diaphot microscope equipped with Nomarski interference contrast optics, and the egg to be injected is immobilized by suction on the end of flame-polished glass holding pipet [Hogan et al., (1986)]. The microinjection needle may be inserted by pressure until the pronucleus is seen to swell. The needle will then be withdrawn, and the procedure repeated on the remaining eggs.

Approximately 500 eggs may be injected as described above, after which approximately 400 will remain viable. The viable eggs may be transferred into the oviducts of pseudopregnant female mice, who will carry then to term [Hogan et al., (1986)]. Approximately 15% of the transferred eggs (60) will develop to term. At three weeks of age, the terminal 1 cm of the tail of each mouse may be removed, and DNA isolated by standard procedures [Hogan et al., (1986)]. The DNAs may be analyzed by Southern blot hybridization, using DNA probes derived from poliovirus receptor genomic or CDNA clones, to determine which of the mice are transgenic, and carry intact copies of the injected gene. Each of these transgenic mice may be used as the founder of a new transgenic strain. For this purpose, each mouse is mated to a normal (non-transgenic) partner, and allowed to produce offspring. Transgenic offspring may be identified by Southern blot analysis of tail DNA.

Construction of Transgenic Mice Expressing PVR: PRG-1 and PRG-3

Cosmids PRG-1 and PRG-3 were cleaved with NotI, and the PVR gene fragment was isolated by gel electrophoresis in low-melt agarose. The DNA fragment was excised from the gel, the agarose melted and the DNA purified by phenol extraction and ethanol precipitation. Ten to twenty micrograms of the DNA were centrifuged to equilibrium in a CsCl gradient, and the fraction containing the DNA was dialyzed for 2–3 days against 10 mM Tris Ph 7.4, 0.2 Mm EDTA, and stored at 20° C.

Fertilized eggs were recovered from female mice that had mated the previous night, by dissecting the oviducts of the pregnant females. The eggs were recovered and stored in medium M2 (Hogan, B. et al., (1986) Manipulating the Mouse Embryo: A Laboratory, Manual, Cold Spring Harbor Laboratory, Cold Spring Harbor). Microinjection needles were prepared from capillary tubing (Clark Electromedical instruments, cat number GC100TF-15) on an automatic pipet puller (David Kopf, Model 700C). The microinjection needles were filled with the DNA solution, and attached to Leitz instrument tube, connected to a pressure injection device (Hogan et al., 1986). The instrument tube was in turn connected to a Leitz micromanipulator, to finely control its movement. The eggs were placed in a depression slide containing medium M2, and viewed under a Nikon Diaphot microscope equipped with Nomarski interference contrast optics, and the egg to be injected was immobilized by suction on the end of flame-polished glass holding pipet (Hogan et al., 1986). The microinjection needle was inserted into the male pronucleus (the larger of the two pronuclei), and DNA was injected by pressure until the pronucleus was seen to swell. The needle was then withdrawn, and the procedure was repeated on the remaining eggs.

Approximately 1000 eggs were injected with each DNA as described above. The viable eggs were transferred into the oviducts of pseudopregnant female mice, who carried them to term (Hogan et al., 1986). At three weeks of age, the terminal 1 cm of the tail of each mouse was removed, and DNA was isolated by standard procedures (Hogan et al., 1986). The DNAs were analyzed by Southern blot hybridization, using DNA probes derived from poliovirus receptor CDNA clones, to determine which of the mice are transgenic, and carry intact copies of the injected gene.

Twenty-one of 54 mice born contained PRG-1 sequences, and 13 out of 37 mice born contained PRG-3 sequences. Southern analysis revealed that each founder mouse contained different numbers of copies of the PVR gene, integrated in head to tail arrays.

Several transgenic founders were mated to normal (nontransgenic) partners, and allowed to produce $F_1$ offspring. Transgenic animals were identified by Southern blot analysis of tail DNA. These mice were used in the studies described below. The following transgenic founders were used: PRG-1-17, male, which contained 10 copies of the PVR gene; PRG-3-6, male, containing 4 copies of the PVR gene; PRG-3-6, male, containing 30 copies of the PVR gene, and PRG-1-7, female, containing 30 copies of the PVR gene.

Northern Blot Analysis of Transgenic Mouse Organ RNA

To determine which transgenic mouse tissues express PVR RNA, a variety of organs were dissected from $F_1$ transgenic mice and RNA was prepared by the guanidine thiocyanate technique (Mendelsohn et al. 1989). The RNAs were subjected to Northern analysis, using a PVR CDNA probe. In transgenic offspring of founders PRG-1-17, PRG-1-7, PRG-3-6 and PRG-3-9, a 3.3 kb PVR RNA was detected in all organs examined, including brain, spinal cord, lung, liver, heart, kidney, intestine, spleen and muscle, although expression in liver was always very low. A 3.3 kb RNA was previously detected in all human tissues examined (Mendelsohn et al. 1989). These results indicate that the PVR gene is expressed in all organs of these transgenic mouse lines.

Poliovirus Binding Assays with Mouse Tissue Homogenates

To determine whether functional PVR is expressed in transgenic mouse tissues, poliovirus binding assays were performed on tissue homogenates. Various organs were dissected from PRG-1-17 $F_1$ transgenic mice, and 5% (w/v) homogenates were prepared in phosphate-buffered saline (PBS). One-tenth ml of homogenates was mixed with 0.01 ml of poliovirus type 1, Mahony strain, and incubated at room temperature for 2 hr. The mixtures were then assayed for infectious poliovirus by plaque assay on HeLa cell monolayers, as described (La Monica et al., (1986) Mapping of Sequences Required For Mouse Neurovirulence of Poliovirus Type 2, Lansing J. Virol. 57:515–525). Binding activity results in a decrease in the number of infectious particles in the mixture. The type 1 Mahoney strain of poliovirus was used for these studies because it is known that this strain does not infect mice, and that mice do not bear receptors for this strain.

Susceptibility of Transgenic Mice to Poliovirus Infection

To determine whether transgenic mice expressing PVR were susceptible to poliovirus infection, two experiments were performed. In the first experiment, 8 transgenic $F_1$ offspring of founder PRG-1-17, and 8 non-transgenic mice were inoculated intracerebrally with $1\times10^5$ plaque-forming units of type 1 Mahoney poliovirus. The mice were observed daily for signs of paralysis. Each day, beginning with the day of inoculation (day 0), at least one transgenic and nontransgenic mouse was sacrificed, the brain and spinal cord removed and homogenized in PBS, and the virus content of the tissue determined by plaque assay on HeLa cell monolayers. The results are shown in FIG. 3.

RESULTS

Secondary Transformants Expressing the Poliovirus Receptor

The subject invention obtained a molecular clone of the poliovirus receptor by employing DNA transformation to transfer susceptibility to poliovirus infection from HeLa cells to mouse L cells. The human receptor gene was identified in the mouse genome by virtue of its linkage to a human Alu repetitive sequence. The isolation of a cell line, CM-1, derived by transformation of L cells with HeLa cell DNA was previously described [Mendelsohn et al., (1986)]. CM-1 cells express poliovirus receptors and are susceptible to infection with all 3 poliovirus serotypes.

CM-1 cells contains a large amount of human DNA, as determined by Southern hybridization analysis using a cloned Alu DNA probe (FIG. 1A, line 1). To eliminate human DNA sequences not necessary for expression of the poliovirus receptor gene, $Ltk^-$ cells were cotransformed with the herpesvirus thymidine kinase gene and genomic DNA prepared from primary transformant CM-1. Five independent poliovirus-susceptible secondary transformants were isolated as described for the CM-1 cell line [Mendelsohn et al., (1986)]. Southern hybridization analysis of genomic DNA from secondary transformants, using the Alu repetitive probe, blur-8, is shown in FIG. 1A. All five cell lines contain a 10 kb BamH I restriction fragment, while all but CM-1.17 contain both 6 kb and 2 kb BamH I fragments. In addition, a 3 kb BamH I fragment is shared by CM-1.17 and CM-1.27. These results indicate that the poliovirus receptor gene contains internal Alu repeat sequences, enabling use of the blur-8 probe for the isolation, from secondary transformants, of genomic clones encoding the poliovirus receptor.

Isolation of Genomic Clones Encoding a Poliovirus Receptor

DNA from the secondary transformant CM-1.24 was used to construct a genomic library in the replacement vector λ2001. Approximately 400,000 bacteriophage plaques were screened with the blur-8 probe, and 3 bacteriophage recombinants containing overlapping DNA inserts were isolated (FIG. 1B). Together the phage inserts span about 30 kb of human genomic DNA. λPVR-4 contains mouse sequence and therefore carries one of the junctions of mouse and human DNA found in CM-1.24. λPVR-2 contains the 6 kb and most of the 10 kb Alu-reactive BamH I fragment which does not react with Alu, but is present in all of the secondary transformants (data not shown).

To identify exon specific probes which hybridized with RNAs only in poliovirus-susceptible cells, restriction fragments from the genomic clones were used as probes in Northern hybridization experiments. The 1 kb BamH I restriction fragment contained in λPVR-2 and λPVR-3 hybridized with a 3.3 kb RNA in HeLa cells and in SY5Y neuroblastoma cells, and with a 3.0 kb RNA in secondary transformant CM-1.9 (FIG. 2A). The shorter size of the RNA in transformants probably results from deletion of 5' and 3' noncoding exons during integration of the receptor sequences in the mouse genome. The 1 kb BamH I fragment did not hybridize with RNA isolated from L cells, which do not express the poliovirus receptor (FIG. 2A).

Isolation of CDNA Clones Encoding a Poliovirus Receptor

To isolate CDNA clones encoding a poliovirus receptor, CDNA libraries were screened with the 1 kb bamH I genomic probe described above. The results of Northern hybridization and nucleotide sequence analysis indicate that four CDNA clones isolated from HeLa cell libraries (HeLa 1.7, HeLa 1.5, H20A and H20B, FIG. 3) represent at least 3 different MRNA species. All four CDNAS share a central 0.85 kb fragment extending from approximately the second EcoR I site through the first Xho I site. This common central fragment is flanked at the 5'-end by either of two different Eco RI fragments, and at the 3'-end by either by two Xho I-EcoR I fragments.

Nucleotide sequence analysis of the two longest CDNA clones, H20A and H20B, indicated the presence, in each, of an open reading frame beginning with a methionine codon within the first EcoR I fragment and ending at a termination codon at two different locations beyond the first Xho I site (FIG. 3). Therefore, H20A and H20B were tested for their ability to direct expression of the poliovirus receptor in transformation experiments. A 1.8 kb Sma I-Bg1 II fragment from H20A and a 2.3 kb Sma I-Bg1 II fragment from H20B were subcloned into the expression vector PSVL, and $Ltk^-$ cells were transformed with either construct or with herring sperm DNA. Forty-eight hours after transformation the cells were infected with poliovirus, and the cell culture medium was assayed for the presence of infectious virus 24 hr later. When L cells transformed with either PSVL-H20A or PSVL-H20B were infected with poliovirus, large numbers of vital progeny were produced (Table 1), confirming that the CDNA clones encode a poliovirus receptor. In contrast, L cells that had been transformed with herring sperm DNA were not susceptible to poliovirus infection. Both PSVL-H20A and PSVL-H20A were also susceptible to poliovirus infection and reacted with anti-receptor monoclonal antibody D171 in situ rosette experiments (data not shown).

TABLE 1

| Yields of poliovirus after infection of mouse cells transformed with poliovirus receptor CDNA clones. | | |
|---|---|---|
| | PFU/ML | |
| Transforming DNA | 0 hours | 24 hours |
| herring sperm | 32 | 37 |
| PSVL-H20A | 9 | $3.4 \times 10^6$ |
| PSVL-H20B | 7 | $3.1 \times 10^6$ |

$Ltk^-$ cells were transformed with the indicated DNAs and 48 hours later were infected with poliovirus type 1. PFU/ml in cell culture medium was determined at 0 and 24 hrs post infection.

To confirm that poliovirus-susceptible transformants containing either PSVL-H20A or PSVL-H20B expressed specific transcripts of the appropriate lengths, RNA from stable L cell transformants was analyzed by Northern hybridization using the 0.97 kb EcoR I fragment of HeLa 1.5 (FIG. 3) as a probe. A 2.4 kb RNA was detected in PSVL-H20A transformants and a major transcript of 2.9 kb was detected in SVL-H20B transformants (FIG. 2B). These are the sizes of RNAs which result from transcription of the receptor CDNAS in PSVL. RNA prepared from L cells transformed with herring sperm DNA did not hybridize to the 0.97 kb probe.

To identify poliovirus receptor MRNAS expressed in HeLa cells and in secondary transformants, the 0.97 kb EcoR I fragment from HeLa 1.5 was hybridized to Northern blots containing poly(A)+RNA prepared from HeLa cells, secondary transformant CM-1.9 and $Ltk^-$ cells (FIG. 2C). The 0.97 kb probe hybridized to a 3.3 kb and a 5.6 kb MRNA in HeLa cells. In the secondary transformant CM-1.9, the 0.85 kb probe hybridized to a single MRNA species of about 3.0 kb (the size difference is visible on a short exposure); no hybridization to poly (A)+RNA from untransformed $Ltk^-$ cells was observed. The presence of a MRNA in CM-1.9 cells which hybridizes to HeLa receptor CDNA indicates that the CDNA encode the receptor gene expressed in secondary transformants.

Additional Northern hybridization analysis (data not shown) was performed to better characterize the pattern of transcription of poliovirus receptor MRNAS. DNA probes derived from both shared and diverged regions of the H20A and H20B CDNAS hybridize with the 3.3 kb MRNA in HeLa cells, indicating that the 3.3 kb MRNA consists of two comigrating species. However, the MRNA represented by the H20B CDNA appears to be less abundant than the MRNA represented by the H20A CDNA. The 5.6 kb MRNA hybridizes to 3'-end sequences present in H20A but not in H20B, indicating that part or all of the H20A sequence is contained in the larger transcript, and that clone H20B is represented only in the 3.3 kb transcript.

Nucleotide Sequence Analysis of Poliovirus Receptor CDNA Clones

The nucleotide and predicted amino acid sequences of functionally active clones H20A and H20B, beginning with the first in-frame methionine codons are shown in FIGS. 4A–4C. The 5'-untranslated sequence shared between the two CDNA clones and the diverged 3'-untranslated sequences are not shown. The CDNA sequence begins with 2 closely packed methionine codons, both of which obey consensus rules for initiation codons, with purines at the −3 and +1 positions with respect to the AUG [Kozak M., Cell. 44:283–292 (1986)]. Following the first methionine is a stretch of 20 uncharged and hydrophobic amino terminal signal sequence. A transmembrane domain, beginning at amino acid residues, typical of an amino acid 344, is composed of 24 hydrophobic and nonpolar amino acids followed by several basic residues. Shortly after the transmembrane domain, the sequences of the two CDNAS diverge, resulting in different amino acid sequences in the cytoplasmic domains. Clone H20B contains a cytoplasmic tail of 25 amino acids in length, while clone H20A contains a 50 amino acid cytoplasmic tail that is rich in serine and threonine residues, possibly a site of phosphorylation. H20A and H20B contain open reading frames of 417 and 392 amino acids, which encode polypeptides of approximately 45,000 and 43,000 daltons, respectively.

The sequences of H20A and H20B diverge from nucleotide 1153 with the cytoplasmic domain, through the 3' ends of the CDNAS. The 5'EcoR I fragment of both CDNAS contains a region of Alu homology beginning at position −29 and ending at −3 with respect to the A in the first initiation codon. The Alu homology begins before the initiating AUGs, indicating that this region is not translated. The 3' noncoding region of H20A, which is approximately 1.9 kb in length, contains a second region of Alu homology beginning at nucleotide 1663 and ending at nucleotide 1700 (sequence not shown). Alu repeat elements have been found in the 3' untranslated domains of several MRNAS including the mouse Class I major histocompatibility antigen [Hood, L., Steinmetz, M. and Malissen, B., Ann. Rev. Immunol. 1:529–568 (1983)], and the low density lipoprotein receptor [Yamamoto, T., Davis, C. G., Brown, M., Schneider, W., Casey, M. L., Goldstein, J. and Russell; D., Cell 39:27–38 (1984)]. The H20B 3'noncoding regions, which is 1.5 kb in length, contains a putative MRNA destabilizing sequence beginning at nucleotide 1702 and ending at nucleotide 1752. The destabilizer sequence consists of several tandom repeats of the sequence ATTTA [Shaw, G. and Kamen, R. Cell. 46:659–667 (1986)]. The presence of this sequence may explain the relatively low level of this RNA in HeLa cells.

The Poliovirus Receptor is a Member of the Immunoglobulin Superfamily

A search of the NBRF protein data base revealed homology between the poliovirus receptor polypeptides and immunoglobulin family members (FIG. 5). The extracellular region of the poliovirus receptor can be folded into a three domain structure (FIG. 6). Each domain contains amino acids which are highly conserved among immunoglobulin family members. These amino acids are with β-strands which can fold into the V1, C1 and C2 domains present in immunoglobulin superfamily members [Williams and Barclay, (1988)]. In particular each of the 3 poliovirus domains contains the conserved cysteine pairs which usually stabilize the structure of the immunoglobulin domains.

The first domain in the poliovirus receptor shows the strongest homology with human Ig lambda chains and to a lesser extent with rat glycoprotein OX-2 and mouse Ig kappa chains (ALIGN scores are shown in the description of FIG. 5). This domain is most likely of the V-type due to the longer distance (73 amino acids) between cysteine residues. The presence of C' and C" β-strands in the V-type domain results in the increased length between cysteine residues. The poliovirus receptor contains a tyrosine at position 86 present in some C' regions of V domains, consistent with classification as a V-type. The homology of domains 2 and 3 with Ig family members is less certain, and therefore amino acid alignments are not shown. However, these domains contain the conserved cysteine and tryptophan residues typical of Ig-like proteins. The highest ALIGN scores generated from comparisons between domain 2 and Ig family members are as follows: 2.47 with human HLA class II histocompatibility antigen, and 1.72 with human Ig gamma constant chain. Homology comparisons with domain 3 did not result in high ALIGN scores with Ig constant or variable regions. However, domain 3 displays significant homology with mouse NCAM domains 3 and 4 (ALIGN scores 7.42 and 5.68, respectively). Since the poliovirus receptor does not have extensive homology with other protein or nucleotide sequences in the Genbank or NBRF data bases, it is probably a new member of the immunoglobulin superfamily.

Expression of Poliovirus Receptor RNA in Human Tissue

An important question is whether expression of poliovirus receptor transcripts in human tissues correlates with the known pattern of poliovirus tissue tropism. Virus replication is limited to a small number of sites in primates, including the oropharyngeal mucosa, the Peyer's patches in the ileum, and motor neurons in the CNS. Replication as well as virus binding activity has not been observed in most other tissues including heart, lung, and kidney [Bodian, (1955); Sabin, A. B., Science 123:1151–1157 (1956); Holland, (1961)].

Figure 7:
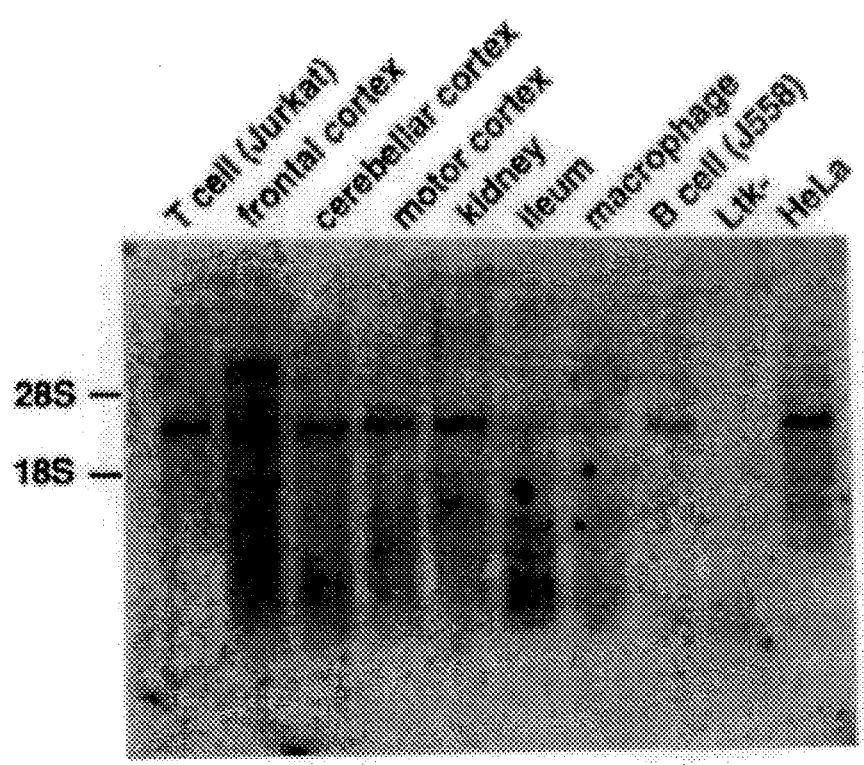

Northern blot hybridization was performed on RNA prepared from human tissues to determine where poliovirus receptor transcripts are expressed. The hybridization probe employed was a 0.4 kb EcoR I-Sma I fragment derived from H20A (FIG. 3), which contains the first 93 amino acids of the predicted protein. A 3.3 kb transcript was detected in HeLa cells and in all the human tissues examined, including frontal cortex, cerebellar cortex, motor cortex, kidney and ileum (FIG. 7). The 3.3 kb MRNA was also detected in cells of the immune system, including cultured B and T cells, and macrophages isolated from human blood. The 0.4 kb probe did not hybridize to RNA isolated from mouse L cells.

Figure 3:
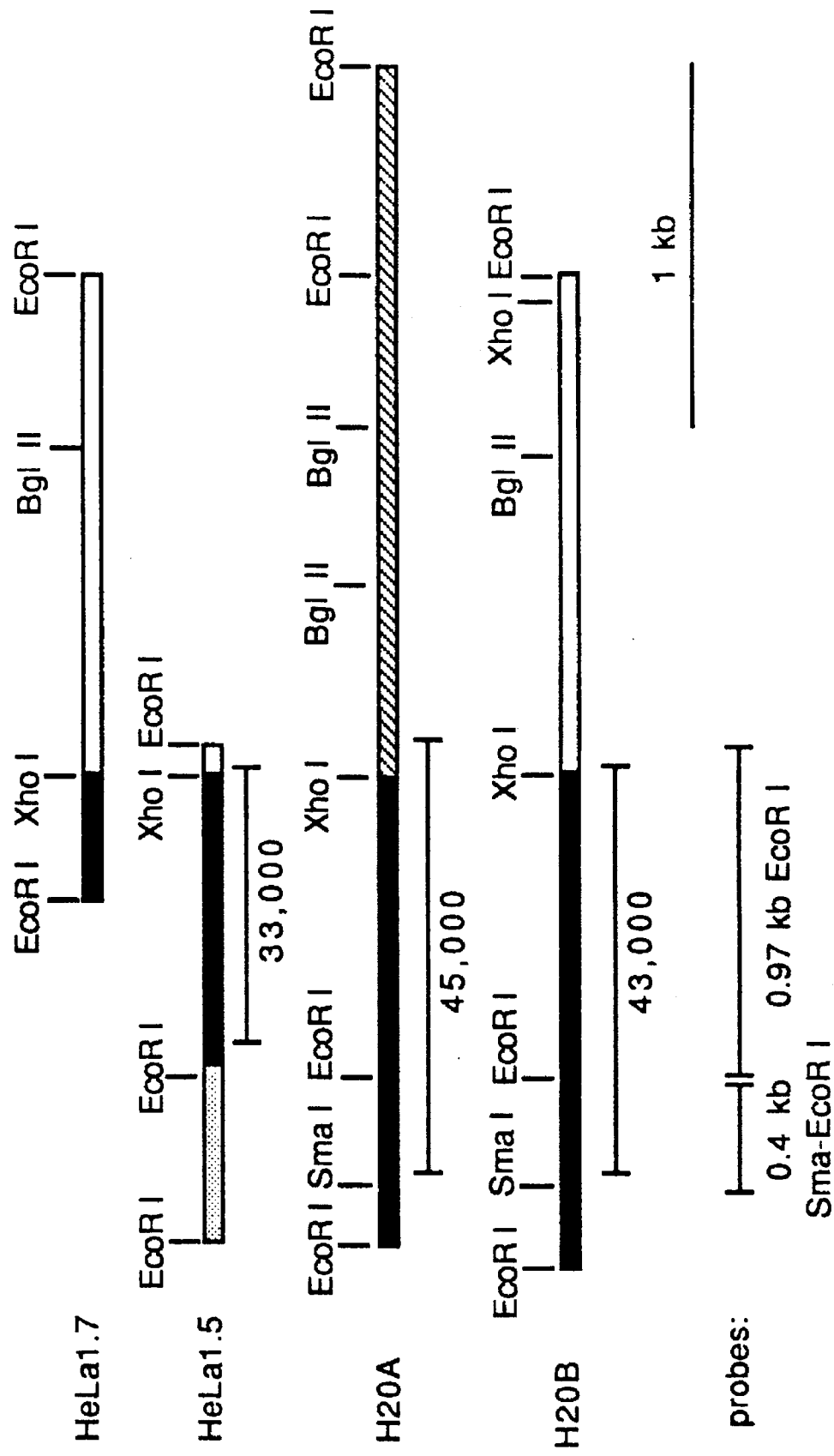
Figure 6:
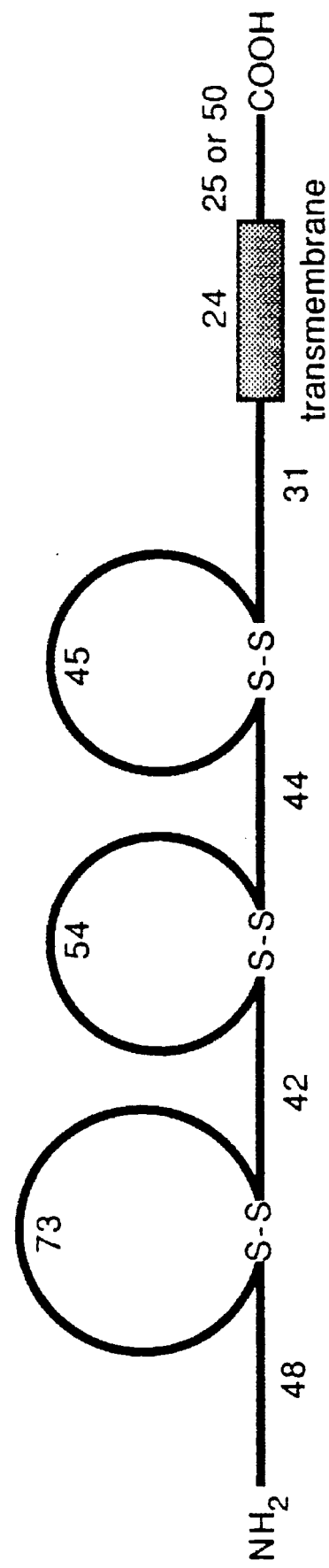

In addition to the 3.3 kb transcript, the 5' probe hybridized to a 5.6 kb RNA present only in the frontal cortex (FIG. 7). In a separate experiment, the same filter was hybridized with the conserved 0.97 kb EcoR I DNA probe (FIG. 3). A pattern of hybridization similar to that found with the 5' probe was observed, except that the 0.4 kb Sma I-EcoR I fragment may be Contained in transcripts which do not include the 0.97 kb EcoR I sequences. Experiments, employing hybridization probes derived from 3'-noncoding regions, suggest tissue-specific expression of RNAs complementary to H20A and H20B (data not shown). Since the poliovirus receptor 3.3 kb transcript is found in the kidney, which is not permissive for poliovirus infection and does not bind poliovirus particles, expression of the 3.3 kb poliovirus receptor RNA is not sufficient to allow infection of tissues by poliovirus.

DNA Binding Assay—Transgenic Mice

Figure 9:
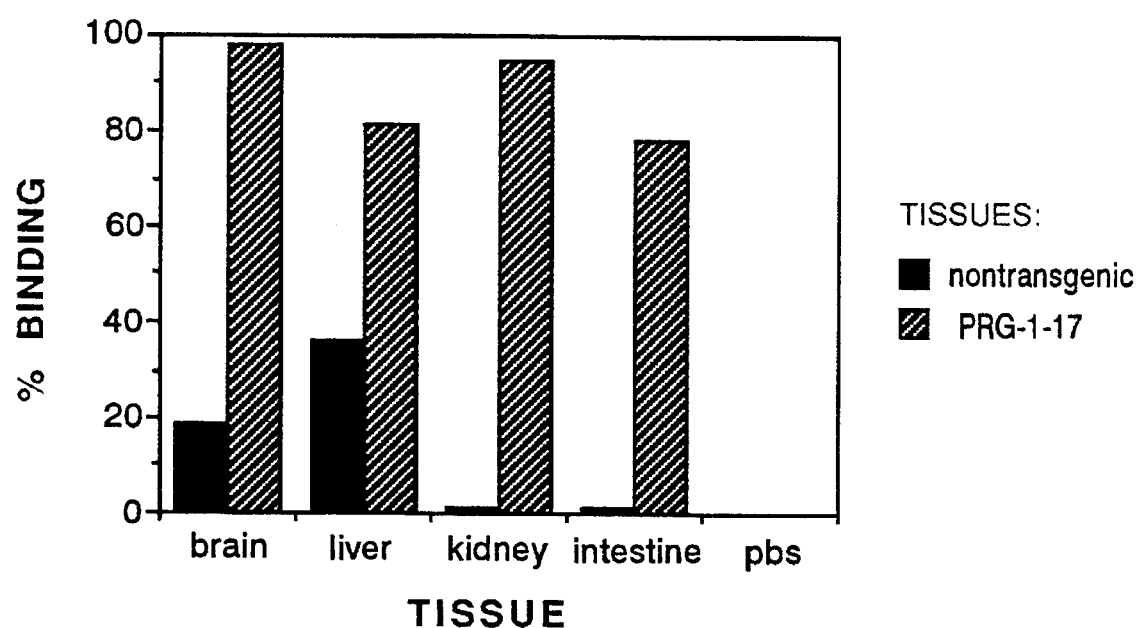

The results of the binding assays are shown in FIG. 9. These results indicate that brain, kidney, intestine and perhaps liver of PRG-1-17 $F_1$ transgenic mice express poliovirus binding sites, and therefore express the PVR transgene in a functional manner. Similar results were obtained for tissue homogenates from $F_1$ transgenic mice of founder PRG-1-7.

Susceptibility of Transgenic Mice to Poliovirus Infection

Figure 10A:
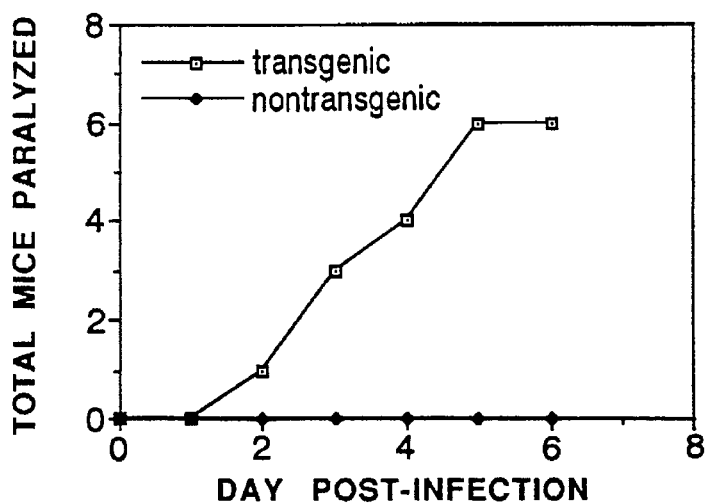
Figure 10B:
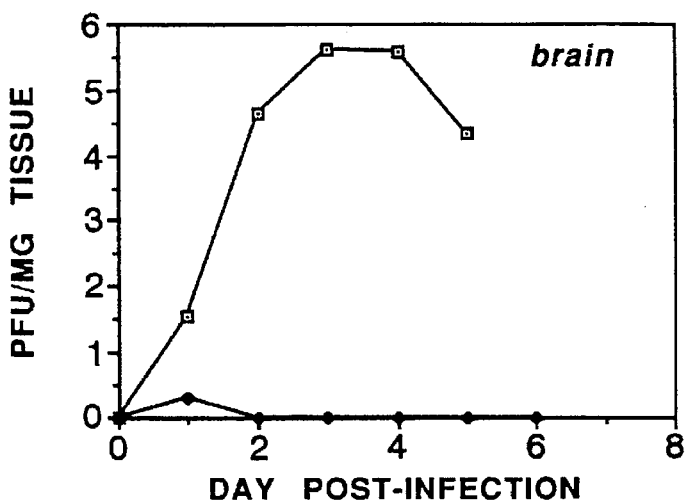
Figure 10C:
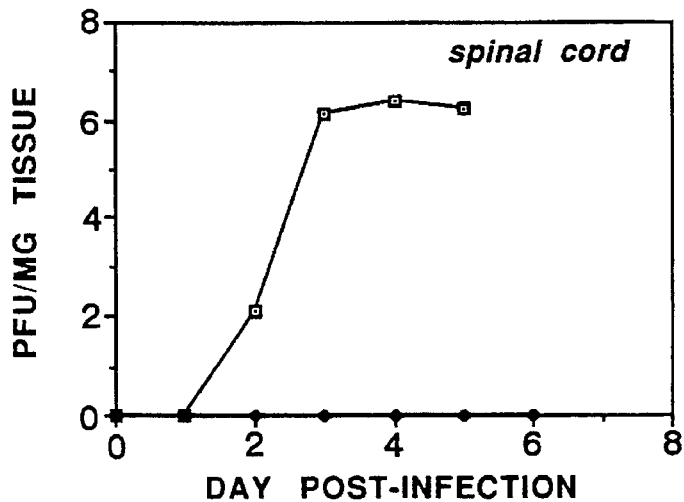

A total of 6 out of 8 transgenic mice inoculated with poliovirus were paralyzed; in contrast, none of the normal (nontransgenic) mice inoculated with virus showed any signs of disease. One mouse was sacrificed on days 0 and 1 for determination of virus titers. This length of time is not enough for development of paralysis; considering that the remainder of the transgenic mice subsequently became paralyzed, it is likely that if the animals had not been sacrificed on days 0 and 1, they would have developed paralytic disease. The transgenic mice showed classic signs of paralytic poliomyelitis-ruffled fur, one or more paralyzed limbs, and tremulous behavior (Jubelt et al., (1980) Pathogenesis of Human Poliovirus Infection In Mice, I Clinical and Pathological Studies, J. Neuropathology, Exp. Neurol. 39:139–148). It is also clear that virus replicates to high titers in the brain and spinal cords of transgenic but not nontransgenic mice (FIGS. 10A–10C). These results indicate that the transgenic mice are susceptible to infection with a poliovirus strain that cannot infect normal mice, and develop a disease that appears to be poliomyelitis.

To determine whether the transgenic mouse expressing the PVR gene could be used for testing of the live, oral poliovaccine, the following experiment was performed. Three transgenic mice of the PRG-1-17 line were inoculated intracerebrally with $5.4 \times 10^5$ pfu of type 1 Mahoney, and 2 transgenic mice were inoculated with the same amount of type 1 Sabin, the oral poliovirus vaccine strain. Four nontransgenic mice were also inoculated with each virus. About two weeks later, two of the mice inoculated with Mahoney had developed paralysis, while none of the mice inoculated with the sabin strain had shown signs of disease. None of the nontransgenic mice inoculated with Mahoney or Sabin showed signs of disease. This experiment confirms that the transgenic mouse expressing PVR is susceptible to infection with poliovirus type 1 Mahoney. Furthermore, the results indicate that the transgenic mice do not develop disease after inoculation with the Sabin 1 strain, an attenuated virus that is part of the live, oral vaccine administered to infants. Currently the poliovirus oral vaccine strains are tested in Cercopithecus monkeys; these animals develop paralysis when inoculated intracerebrally or intraspinally with neurovirulent strains of poliovirus, such as type 1 Mahoney, but do not develop disease after inoculation with attenuated strains such as Sabin 1. The results with the transgenic mice expressing the PVR gene suggest that this mouse model may be suitable for the testing of poliovirus oral vaccine strains, and perhaps for the development of new poliovirus vaccine strains.

Discussion

This invention describes the isolation of functional CDNA clones encoding cellular receptors for poliovirus. Primary and secondary mouse cell transformants were obtained, after transformation of L cells with HeLa cell DNA, which express the human poliovirus receptor at the cell surface and are sensitive to infection with all 3 poliovirus serotypes. The human receptor gene was rescued from the genome of mouse cell transformants by probing genomic libraries with a human repetitive probe. Probes derived from the poliovirus receptor genomic clones were then used to isolate two receptor CDNA clones from HeLa cells, which encode functional poliovirus receptor is a member of the immunoglobulin family of cell surface molecules.

The Poliovirus Receptor is Encoded by Multiple RNAs

The results of Northern blot experiments indicates that HeLa cells contain at least 3 transcripts which hybridize to the poliovirus receptor CDNAS: a 5.6 kb RNA and two RNAs that comigrate at about 3.3 kb. The H20A and H20B CDNA clones probably represent the 3.3 kb MRNAS. The origin of the 5.6 kb HeLa MRNA is not clear, although this RNA hybridizes to coding and 3' noncoding probes derived from the H20A CDNA but not from 3'- noncoding probes from the H20B CDNA (data not shown). These results indicate that the 5.6 kb RNA contains H20A sequences as well as additional sequences that have not been claimed.

It is likely that transcripts represented by H20A and H20B arise from a single gene. In Southern hybridization experiments, probes derived from the 3'- end of both CDNAS hybridize to a single restriction fragment in HeLa cells as well as in secondary transformants that express the poliovirus receptor (data not shown). Since the transformants contain approximately 30 kb of human DNA, based on their content of Alu-reactive sequences, it is unlikely that two separate receptor genes give rise to H20A and H20B transcripts, unless the genes are very tightly linked. Alternative splicing of 3' exons or use of different 3 polyadenylation sites can account for the structures of MRNAS represented by the H20A and H20B CDNA clones, which contain different cytoplasmic tails as well as diverged 3' noncoding sequences.

The destabilizer sequence present in the 3' end of the H20B CDNA may function as a post transcriptional regulatory mechanism in certain cell types. This idea is supported by the observation that levels of the H20B MRNA are low in HeLa cells compared to the high levels of the H20A message, which does not contain the destabilizer sequence. However, other mechanisms might also regulate levels of the two RNAs.

Expression of Poliovirus Receptor MRNA and Poliovirus Tissue Tropism

To determine if expression of the poliovirus receptor gene follows the same pattern reported for poliovirus binding activity, human tissue was examined for expression of poliovirus receptor transcripts. The results indicate that expression of the binding site for poliovirus is probably regulated by post transcriptions events. For example, Northern hybridization experiments indicate the presence of a 3.3 kb RNA in human kidney which hybridized with both coding and 3'- noncoding probes derived from the poliovirus receptor CDNAS. Since the kidney is not a site of poliovirus replication and does not contain detectable poliovirus binding activity, it is concluded that expression of poliovirus receptor MRNA is insufficient to encode functional receptor activity in this tissue.

There are several reasons why a receptor MRNA expressed in kidney might not lead to detectable poliovirus binding activity. It is possible that the receptor MRNA observed in kidney is not translated into protein. Alternatively, the MRNA expressed in kidney might encode a protein that cannot bind poliovirus due to differences in the amino acid sequence. Expression of poliovirus receptor sites in tissues might also be dependent on post translational modification. For example, the developmentally regulated addition of negatively charged α-2,8-linked polysialic acid to a site outside the ligand binding region is thought to play a major role in regulation of NCAM binding activity [Edelman, G., Ann. Rev. Cell. Biol. 2:81–116 (1986)]. Other types of post translational modification, such as phosphorylation and sulfation of N-linked oligosaccharides, are also thought to be involved in regulation of NCAM activity and expression [Edelman, 1986; Cunningham, B., Hemperly, J., Murray, B., Prediger, E., Brackenbury, R., Edelman, G., Science 236:799–806 (1987)].

Another possibility is that a functional poliovirus receptor consists of the 45K polypeptide associated with other membrane proteins. For example, there are 2 classes of interleukin-2 binding sites present on T lymphocytes, a low affinity site and a high affinity site [Robb, R., Green, W. and Rusk, C., J. Exp. Med. 160:1126 (1984)]. Transformation experiments indicate that cloned IL-2 receptor CDNAS encode only the low affinity binding site [Green W., Robb, R. Svetlik, P., Rusk, C., Depper, J. and Leonard, W. J. Exp. Med. 162:363–368 (1985)]. The association of a second protein with the low affinity IL-2 receptor subunit is necessary to create a high affinity IL-2 binding site [Sharon M., Klausher, R., Cullen, B., Chizzonite, R. and Leonard, W., Science 234 859–863 (1986)]. Perhaps high-affinity binding of poliovirus is mediated by a similar mechanism.

Since poliovirus is not the natural ligand of the receptor that we have cloned, the regulation of the binding site is probably important for the natural function of this receptor. If the receptor participates in cell recognition or adhesion, as do other members of the immunoglobulin family, it might be expected that expression of the activity of this protein would be tightly regulated, both in a development and tissue specific fashion.

It is known that tissues such as kidney and amnion, which do not express binding sites for poliovirus, can be induced to express receptor activity by dispersion of the tissues and subsequent culture in vitro [Holland, (1961)]. If expression of the poliovirus binding site is regulated by post translational modification of the receptor protein, the modification might be induced by culturing organs or tissues in vitro. Alternatively, ancillary proteins required for virus binding activity might be induced by in vitro culturing.

The Poliovirus Receptor is a Member of the Immunoglobulin Superfamily

Protein homology comparisons revealed regions of amino acid conservation between the poliovirus receptor and members of the immunoglobulin family. The poliovirus receptor is a third known member of the immunoglobulin family which functions as a virus receptor. The CD4 receptor expressed on cells of the immune system has been shown to be the receptor for HIV-1, the causative agent of AIDS [Maddon et al., (1986)]. Intercellular adhesion molecule 1 (ICAM-1), which widely expressed in human tissues, is the major rhinovirus receptor (Greve and McCelland, personal communication). An interesting question is whether the domain structure common to molecules of the immunoglobulin family is a common feature of proteins that mediate the entry of certain viruses in cells, or simply reflects the fact that many cell surface molecules are Ig-like. It should be noted that known receptors for several other viruses, such as influenza virus and Epstein-Barr virus, are immunoglobulin family members [Weis W., Brown, J. H., Cusack, S., Paulson, J. C. Skehel, J. J. and Wiley, D. C., Nature 333:426–431 (1988); Fingeroth J. D., Weis, J. J., Tedder, T. F., Strominger, J. L., Biro, A. P., and Fearon, D. T. Proc. Natl. Acad. Sci. USA 81:4510–4514 (1984)].

Atomic structures for poliovirus type 1 and rhinovirus type 14 reveal a common cleft in the virion, called the "canyon", which encircles each of the 12 vertices of the iscosahedral capsid [Rossman M. G., Arnold, E., Erickson, J. W., Frankenberger, E. A., Griffith, J. P. Hect, H. J., Johnson, J. E. and Kramer, D. J. Science 229:1368–1365 (1985). This cleft has been proposed to be the site on the virion that attaches a cellular receptor [Rossman et al., (1985)]. It has been suggested that the relative inaccessibility of the canyon to the host immune system allows the virus to maintain such a binding site free from the evolutionary pressure generated by most neutralizing antibodies. Surrounding the canyon are promontories formed by exposed loops of amino acids, whose sequences are relatively variable and which contain some of the well characterized antigenic sites associated with different viral serotypes [Hogle et al., (1985)]. Mutations introduced into the walls and floor of the rhinovirus canyon alter the affinity of the virus binding, supporting the canyon as the receptor binding site [Colonno R., Condra, J., Mizutani, S., Callahan, P., Davies, M. and Murcko, M. Proc. Natl. Acad. Sci. USA 85:5453–6559 (1988)]. Since both poliovirus and rhinovirus use receptors that are Ig-like, it is tempting to speculate that the picornavirus canyon is particularly suited to attach to the domain structure of Ig-like molecules. Identification of additional picornavirus receptors will be required to address this question. It will also be of interest to determine whether the CD4 binding site on gp120 of HIV is also a canyon-like structure.

Poliovirus is believed to enter cells by receptor-mediated endocytosis, with a low Ph phase required for virion uncoating [Madshus, I. H., Olsnes, S. and Sandvig, K. J. Cell. Biol. 98:1194–1200 (1984)]. The availability of a functional, cloned copy of a poliovirus receptor will enable analysis, by site-directed mutagenesis, of regions of the receptor required not only for virus binding but for entry and uncoating. It may also be possible to solve the atomic structure of the receptor polypeptide as well as the virus-receptor complex. Together the results between virus and its cellular receptor, knowledge of which may be crucial for designing future antiviral strategies.

It will also be important to identify the natural function of the poliovirus receptor. Many members of the Ig family participate in cellular recognition and adhesion, and the functional CDNAS of the subject invention may be used to determine whether the poliovirus receptor is capable of mediating these activities.

What is claimed is:

1. A transgenic mouse which has stably integrated into the genome of its somatic and germ cells the DNA sequence H20A of FIG. 4 which encodes a human poliovirus receptor, wherein expression of said DNA sequence results in the mice becoming susceptible to poliovirus infection.

2. A transgenic mouse which has stably integrated into the genome of its somatic and germ cells the DNA sequence H20B of FIG. 4 which encodes a human poliovirus receptor, wherein expression of said DNA sequence results in the mice becoming susceptible to poliovirus infection.

3. A method of producing a transgenic mouse which expresses a human poliovirus receptor comprising:
   a. introducing the DNA sequence H20A of FIG. 4 operatively linked to a promoter into a fertilized mouse egg;
   b. transferring the fertilized egg containing said DNA sequence to the oviduct of a pseudopregnant female mouse wherein the mouse becomes pregnant;
   c. allowing the pregnant female mouse to deliver progeny mice; and
   d. selecting from the progeny mice those which have stably incorporated into the genome the DNA sequence H20A.

4. A method of producing a transgenic mouse which expresses a human poliovirus receptor comprising:
   a. introducing the DNA sequence H20B of FIG. 4 operatively linked to a promoter into a fertilized mouse egg;
   b. transferring the fertilized egg containing said DNA sequence to the oviduct of a pseudopregnant female mouse wherein the mouse becomes pregnant;
   c. allowing the pregnant female mouse to deliver progeny mice; and
   d. selecting from the progeny mice those which have stably incorporated into the genome the DNA sequence H20B.

5. A method of testing the virulence of a human poliovirus vaccine which comprises administering the vaccine to the transgenic mouse of claim 1 and determining the physiological effect of the vaccine on the transgenic mouse.

6. The method of claim 5, wherein the physiological effect is paralysis.

7. A method of testing the virulence of a human poliovirus vaccine which comprises administering the vaccine to the transgenic mouse of claim 2 and determining the physiological effect of the vaccine on the transgenic mouse.

8. The method of claim 7, wherein the physiological effect is paralysis.

* * * * *